US012558443B2

(12) United States Patent
Childress et al.

(10) Patent No.: US 12,558,443 B2
(45) Date of Patent: Feb. 24, 2026

(54) PORTABLE SANITIZING SYSTEMS AND METHODS HAVING MODULAR COMPONENTS

(71) Applicant: THE BOEING COMPANY, Chicago, IL (US)

(72) Inventors: Jamie J. Childress, Mercer Island, WA (US); Kevin S. Callahan, Everett, WA (US); Douglas Alan Brown, Edmonds, WA (US)

(73) Assignee: The Boeing Company, Arlington, VA (US)

( * ) Notice: Subject to any disclaimer, the term of this patent is extended or adjusted under 35 U.S.C. 154(b) by 1154 days.

(21) Appl. No.: 17/514,001

(22) Filed: Oct. 29, 2021

(65) Prior Publication Data

US 2022/0047746 A1      Feb. 17, 2022

Related U.S. Application Data

(63) Continuation-in-part of application No. 17/026,417, filed on Sep. 21, 2020, now Pat. No. 11,793,896.

(60) Provisional application No. 63/123,517, filed on Dec. 10, 2020, provisional application No. 63/054,985, filed on Jul. 22, 2020.

(51) Int. Cl.
| | |
|---|---|
| *A61L 2/10* | (2006.01) |
| *A61L 2/24* | (2006.01) |
| *B64F 5/30* | (2017.01) |

(52) U.S. Cl.
CPC .................. *A61L 2/10* (2013.01); *A61L 2/24* (2013.01); *A61L 2202/11* (2013.01); *A61L 2202/14* (2013.01); *A61L 2202/15* (2013.01);

*A61L 2202/16* (2013.01); *A61L 2202/25* (2013.01); *B64F 5/30* (2017.01)

(58) Field of Classification Search
CPC ..................................... A61L 2/10; A61L 2/24
See application file for complete search history.

(56) References Cited

U.S. PATENT DOCUMENTS

| | | | | |
|---|---|---|---|---|
| 5,920,075 | A | * | 7/1999 | Whitehead ................ A61L 2/10 |
| | | | | 250/492.1 |
| 2014/0264084 | A1 | | 9/2014 | Davis |
| 2018/0193502 | A1 | * | 7/2018 | Ufkes .................... A61B 90/70 |

(Continued)

FOREIGN PATENT DOCUMENTS

| | | |
|---|---|---|
| CN | 108904833 | 11/2018 |
| CN | 109199708 | 1/2019 |
| CN | 209060084 | 7/2019 |

(Continued)

OTHER PUBLICATIONS

Extended European Search Report for EP 21213030.5-1101, dated Jul. 1, 2022.

(Continued)

*Primary Examiner* — Sean E Conley

(74) *Attorney, Agent, or Firm* — Joseph M. Butscher; Carroll, Hoette & Butscher, LLC

(57) ABSTRACT

A portable sanitizing system and method include a wand assembly including a sanitizing head having an ultraviolet (UV) lamp. A container includes an internal chamber. The wand assembly is coupled to the container. One or more component modules are configured to be removably secured within the internal chamber.

24 Claims, 25 Drawing Sheets

(56) References Cited

U.S. PATENT DOCUMENTS

2020/0087031 A1 *   3/2020   Yoo ........................ A45D 44/00

FOREIGN PATENT DOCUMENTS

| | | |
|---|---|---|
| CN | 209564419 | 11/2019 |
| CN | 111388100 | 7/2020 |
| CN | 211048664 | 7/2020 |
| CN | 211535762 | 9/2020 |
| DE | 102017107210 | 10/2018 |

OTHER PUBLICATIONS

Partial European Search Report for EP 21213030.5-1101, dated Apr. 12, 2022.

* cited by examiner

105

190

190

104

170

192

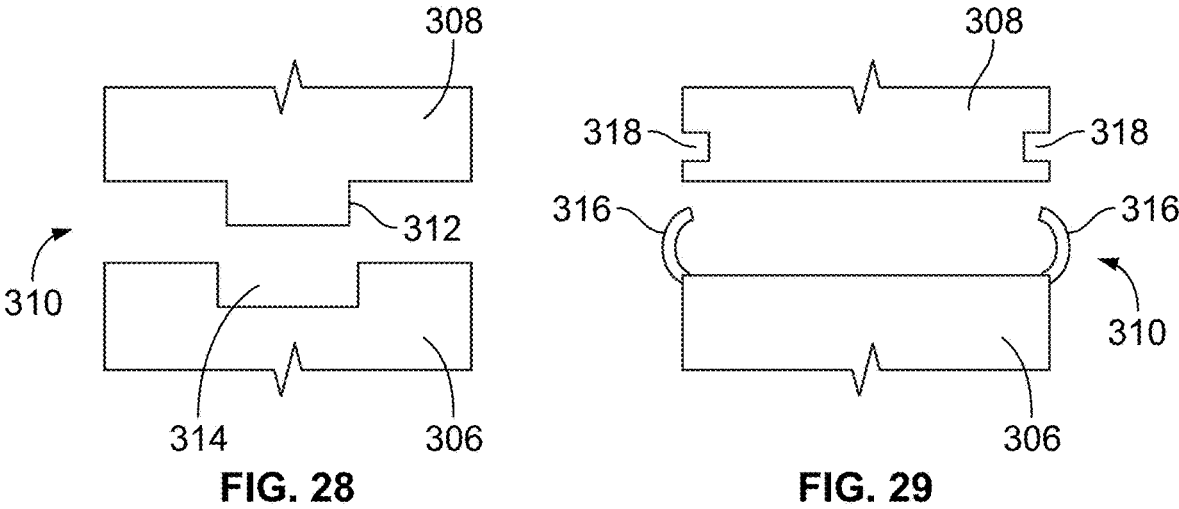
FIG. 28
FIG. 29
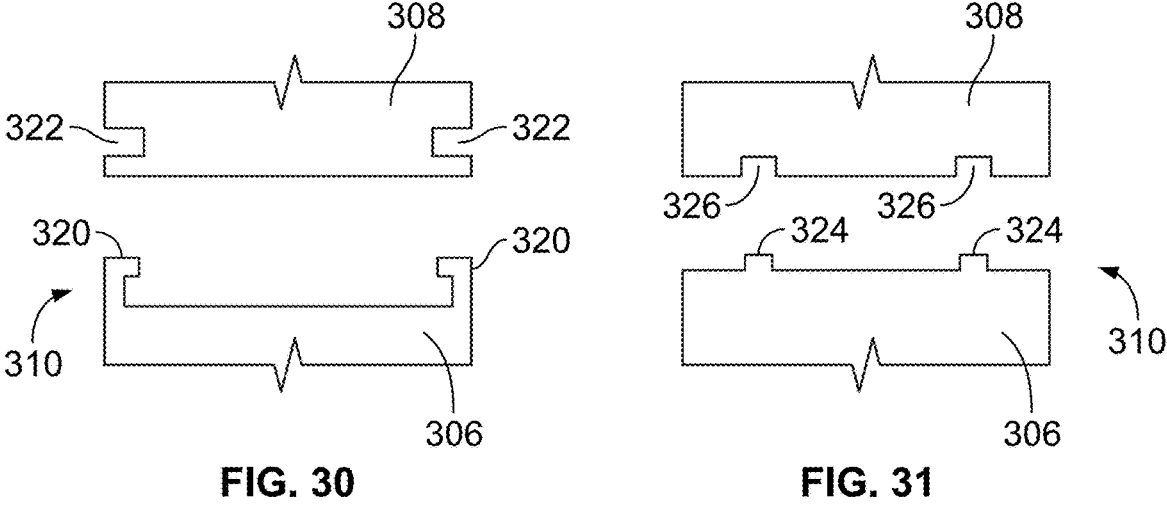
FIG. 30
FIG. 31

1436

1430

1432

1434

1431

Coupling a wand assembly to a container
including an internal chamber          500

Removably securing one or more component
modules within the internal chamber          502

PORTABLE SANITIZING SYSTEMS AND METHODS HAVING MODULAR COMPONENTS

RELATED APPLICATIONS

This application is a continuation-in-part of U.S. patent application Ser. No. 17/026,417, entitled "Portable Sanitizing Systems and Methods," filed Sep. 21, 2020, which is hereby incorporated by reference in its entirety.

U.S. patent application Ser. No. 17/026,417, in turn, relates to and claims priority benefits from U.S. Provisional Patent Application No. 63/054,985, entitled "Portable Sanitizing Systems and Methods," filed Jul. 22, 2020.

This application also relates to and claims priority benefits from U.S. Provisional Patent Application No. 63/123,517, entitled "Portable Sanitizing Systems and Methods Having Modular Components," filed Dec. 10, 2020, which is hereby incorporated by reference in its entirety.

FIELD OF THE DISCLOSURE

Embodiments of the present disclosure generally relate to sanitizing systems, such as may be used to sanitize structures and areas within vehicles, such as commercial aircraft.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light. In order to sanitize a surface of a structure, a known UV light sterilization method emits a broad spectrum UVC light onto the structure.

Further, known UV light sanitizing systems are typically large, bulky, and often require fixed, stationary infrastructure.

Additionally, UV light sanitizing systems include numerous components. If one of the components is in need of repair or replacement, the process of replacing the component is time and labor intensive. Moreover, when replacing or repairing the component, there is a potential of inadvertently damaging other components. As such, when a particular component of a system malfunctions, the entire system may be discarded and replaced, as the repair or replacement may exceed the cost of an entirely new system.

SUMMARY OF THE DISCLOSURE

A need exists for a UV sanitizing system and method in which component parts can be quickly and easily repaired or replaced, when needed. Further, a need exists for a UV sanitizing system that can be easily adapted for different needs.

With those needs in mind, certain embodiments of the present disclosure provide a portable sanitizing system including a wand assembly including a sanitizing head having an ultraviolet (UV) lamp. A container includes an internal chamber. The wand assembly is coupled to the container. One or more component modules are removably secured within the internal chamber.

As an example, the container is a case assembly. As another example, the container is a backpack assembly.

In at least one embodiment, the one or more component modules include a power supply, a battery pack, or a blower. Further, the one or more component modules can also include the wand assembly.

In at least one embodiment, the container also include one or more receptacles within the internal chamber. The one or more component modules are configured to removably secure to the one or more receptacles through one or more coupling interfaces. As an example, the one or more coupling interfaces include a plug and a socket, one or more latches, one or more detents, or one or more snaps.

In at least one embodiment, the container also include a radio frequency identification (RFID) tag.

In at least one embodiment, the container also includes a global positioning system (GPS) device.

In at least one embodiment, the system also includes a retaining frame secured to the container. The retaining frame is configured to house one or more additional component modules.

In at least one embodiment, the container also includes a window that is configured to allow viewing into at least a portion of the internal chamber.

In at least one embodiment, the one or more component modules includes a power supply. The power supply includes an activation switch and an information screen. Status indicators are displayed on the information screen.

In at least one embodiment, the container further includes a microcontroller configured to detect information regarding the one or more component modules.

In at least one embodiment, the system further includes a hose that connects the wand assembly to the container. The hose includes a first connector that removably connects to a second connector of the container.

Certain embodiments of the present disclosure provide a portable sanitizing method, including coupling a wand assembly to a container including an internal chamber. The wand assembly includes a sanitizing head having an ultraviolet (UV) lamp. The method also includes removably securing one or more component modules within the internal chamber.

BRIEF DESCRIPTION OF THE DRAWINGS

FIG. 28 illustrates a simplified view of a coupling interface between a component module and a receptacle, according to an embodiment of the present disclosure.

FIG. 29 illustrates a simplified view of a coupling interface between a component module and a receptacle, according to an embodiment of the present disclosure.

FIG. 30 illustrates a simplified view of a coupling interface between a component module and a receptacle, according to an embodiment of the present disclosure.

FIG. 31 illustrates a simplified view of a coupling interface between a component module and a receptacle, according to an embodiment of the present disclosure.

DETAILED DESCRIPTION OF THE DISCLOSURE

Figure 1:
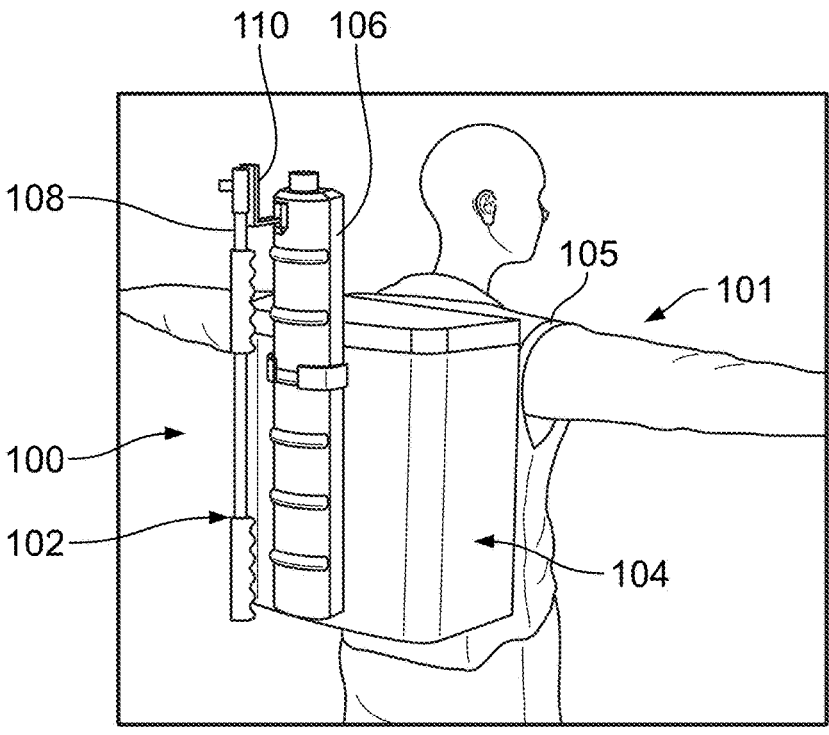
FIG. 1 illustrates a perspective view of a portable sanitizing system worn by an individual, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a sanitizing system that includes a container (such as a case assembly, a backpack assembly, a cart assembly, or the like) that contains a plurality of component modules. Examples of the component modules include a battery pack, a power supply, a blower fan, a wand assembly with a hose attachment, and the like. The component modules are configured to be removably secured within the container. As such, the component modules can be quickly and easily removed, repaired outside of the container, and/or replaced with another component module. Further, the component modules can be removed from a first container, such as of a case assembly, a backpack assembly, or a cart assembly, and inserted into a second container that differs from the first container, such as another one of a case assembly, a backpack assembly, or a cart assembly. Embodiments of the present disclosure provide modularity and ease of repair of portions of the UV sanitizing system.

In at least one embodiment, the UV wand assembly and/or a hose assembly can be quickly and easily unplugged from a power module, and plugged into an alternative power module without the use of tools. The UV wand assembly and hose assembly can be plugged into a power module of a backpack assembly, a roller bag. A shoulder bag, a fixed location, and/or the like.

In at least one embodiment, the UV sanitizing system also includes a microcontroller that is configured to detect component status and compatibility. The is configured to adjust system parameters based on configuration. The microcontroller can display a status light and optional informational display message to provide status information, such as fault conditions, diagnostic data, and battery state. In at least one embodiment, the microcontroller is configured to detect the make and model of attached accessories, based on a connector pin arrangement. The microcontroller compares the installed pin arrangement data to known arrangements to determine compatibility of the accessory, and may adjust the system parameters to optimize the system.

In at least one embodiment, the hose connecting the UV wand to the system may be attached to the system with a threaded retainer, and may contain a wire strain relief retainer inside the hose to prevent high voltage wires from detaching during the removal and replacement process.

Embodiments of the present disclosure provide plug and play modularity for components of a UV sanitizing system to allow for easier removal and replacement of components. The component modules can be inserted and removed from a container (such as a backpack assembly, case assembly, cart, or the like) without the use of tools.

In at least one embodiment, the UV sanitizing system can be tracked and monitored via a global positioning system (GPS)-enabled asset management system. The asset management system can provide geographic location wirelessly to a control center and/or one or more handheld devices, such as smart phones, smart tablets, laptop computers, or other computing devices.

FIG. 1 illustrates a perspective view of a portable sanitizing system 100 worn by an individual 101, according to an embodiment of the present disclosure. The portable sanitizing system 100 includes a wand assembly 102 coupled to a backpack assembly 104 that is removably secured to the individual through a harness 105. The wand assembly 102 includes a sanitizing head 106 coupled to a handle 108. In at least one embodiment, the sanitizing head 106 is moveably coupled to the handle 108 through a coupler 110.

In at least one other embodiment, the portable sanitizing system 100 may not be worn by the individual 101. For example, the portable sanitizing system 100 may include a case assembly that is configured to be opened and closed. The case assembly may store the wand assembly 102 when not in use. The case assembly may be opened to allow the wand assembly 102 to be removed and operated.

As shown in FIG. 1, the wand assembly 102 is in a stowed position. In the stowed position, the wand assembly 102 is removably secured to a portion of the backpack assembly 104, such as through one or more tracks, clips, latches, belts, ties, and/or the like.

In at least one other embodiment, the wand assembly 102 is stored within a case assembly in a stowed position. For example, the wand assembly 102 in the stowed position is contained within a closed case assembly. The case assembly may be opened to allow the wand assembly 102 to be removed and deployed.

Figure 2:
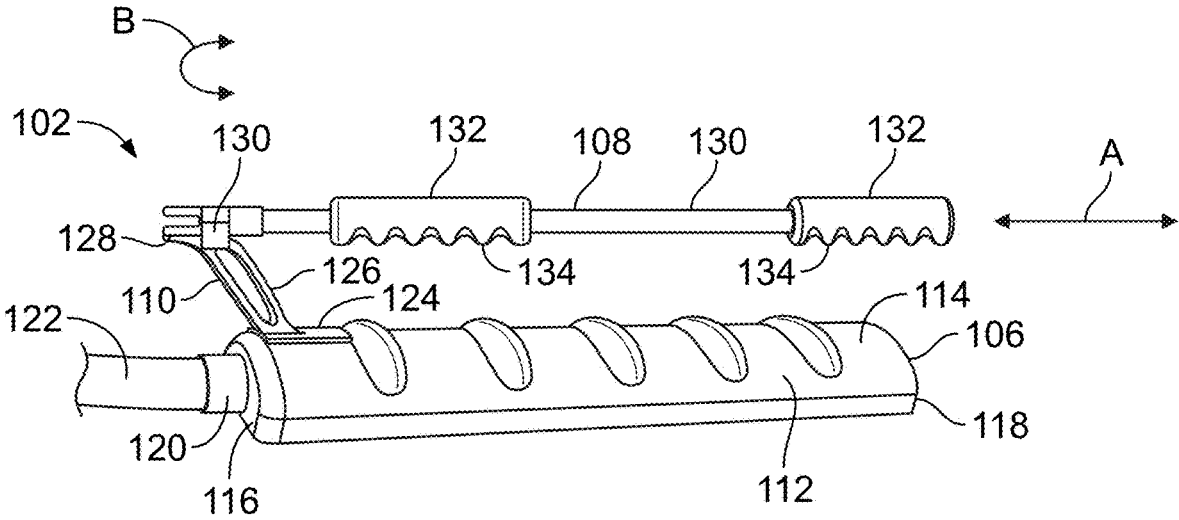
FIG. 2 illustrates a perspective lateral top view of a wand assembly, according to an embodiment of the present disclosure.

FIG. 2 illustrates a perspective lateral top view of the wand assembly 102, according to an embodiment of the present disclosure. The sanitizing head 106 couples to the handle 108 through the coupler 110. The sanitizing head 106 includes a shroud 112 having an outer cover 114 that extends from a proximal end 116 to a distal end 118. As described herein, the shroud 112 contains a UV lamp.

Optionally, the wand assembly 102 may include the sanitizing head 106 connected to a fixed handle. Further, the wand assembly 102 may be sized and shaped differently than shown.

A port 120 extends from the proximal end 116. The port 120 couples to a hose 122, which, in turn, couples to the backpack assembly 104 (shown in FIG. 1). The hose 122 contains electrical cords, cables, wiring, or the like that couples a power source or supply (such as one or more batteries) within the backpack assembly 104 (shown in FIG. 1) to a UV lamp 140 within the shroud 112. Optionally, the electrical cords, cables, wiring, or the like may be outside of the hose 122. In at least one embodiment, the hose 122 also contains an air delivery line, such as an air tube) that fluidly couples an internal chamber of the shroud 112 to an air blower, vacuum generator, air filters, and/or the like within the backpack assembly 104.

The coupler 110 is secured to the outer cover 114 of the shroud 112, such as proximate to the proximal end 116. The coupler 110 may include a securing beam 124 secured to the outer cover 114, such as through one or more fasteners, adhesives, and/or the like. An extension beam 126 outwardly extends from the securing beam 124, thereby spacing the handle 108 from the shroud 112. A bearing assembly 128 extends from the extension beam 126 opposite from the securing beam 124. The bearing assembly 128 includes one or more bearings, tracks, and/or the like, which allow the handle 108 to linearly translate relative to the coupler 110 in the directions of arrows A, and/or pivot about a pivot axle in the directions of arc B. Optionally, the securing beam 124 may include a bearing assembly that allows the sanitizing head 106 to translate in the directions of arrows A, and/or rotate (for example, swivel) in the directions of arc B in addition to, or in place of, the handle 108 being coupled to the bearing assembly 128 (for example, the handle 108 may be fixed to the coupler 110).

In at least one other embodiment, the wand assembly 102 does not include the coupler 110. Instead, the handle 108 may be fixed to the shroud 112, for example.

In at least one embodiment, the handle 108 includes a rod, pole, beam, or the like 130, which may be longer than the shroud 112. Optionally, the rod 130 may be shorter than the shroud 112. One or more grips 132 are secured to the rod 130. The grips 132 are configured to be grasped and held by an individual. The grips 132 may include ergonomic tactile features 134.

Optionally, the wand assembly 102 can be sized and shaped differently than shown. For example, in at least one example, the handle 108 can be fixed in relation to the shroud 112. Further, the handle 108 may not be configured to move relative to itself and/or the shroud 112. For example, the handle 108 and the shroud 112 can be integrally molded and formed as a single unit.

Figure 3:
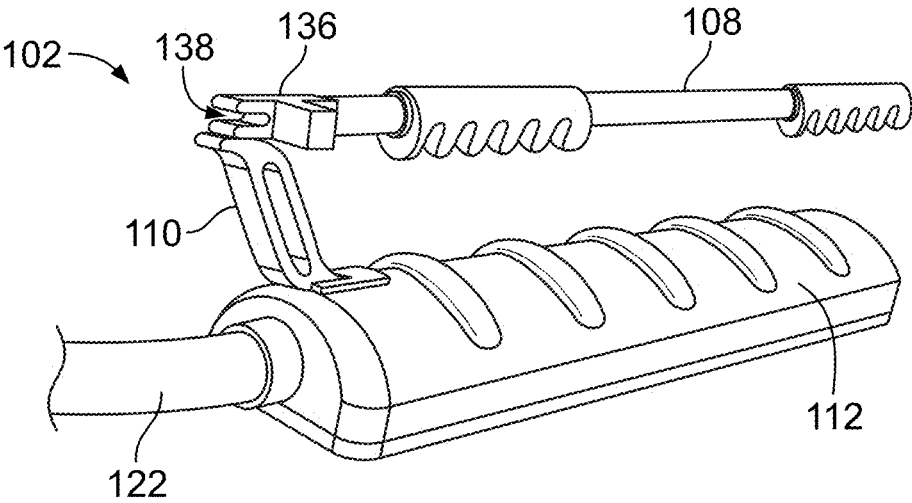
FIG. 3 illustrates a perspective rear view of the wand assembly of FIG. 2.
Figure 4:
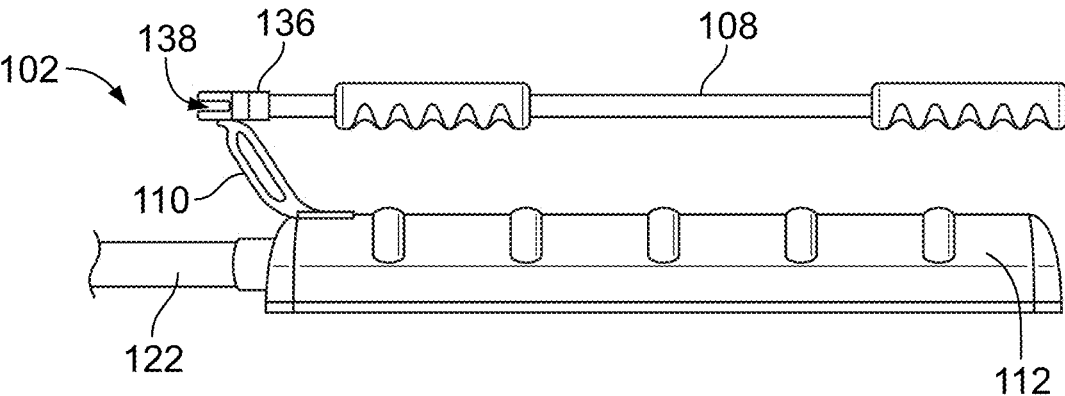
FIG. 4 illustrates a perspective lateral view of the wand assembly of FIG. 2.

FIG. 3 illustrates a perspective rear view of the wand assembly 102 of FIG. 2. FIG. 4 illustrates a perspective lateral view of the wand assembly 102 of FIG. 2. Referring to FIGS. 3 and 4, the handle 108 may pivotally couple to the coupler 110 through a bearing 136 having a pivot axle 138 that pivotally couples the handle 108 to the coupler 110. The handle 108 may further be configured to linearly translate into and out of the bearing 136. For example, the handle 108 may be configured to telescope in and out. Optionally, or alternatively, in at least one embodiment, the handle 108 may include a telescoping body that allows the handle 108 to outwardly extend and inwardly recede. In at least one other embodiment, the handle 108 may not be configured to move, extend, retract, or the like relative to the shroud 112.

Figure 5:
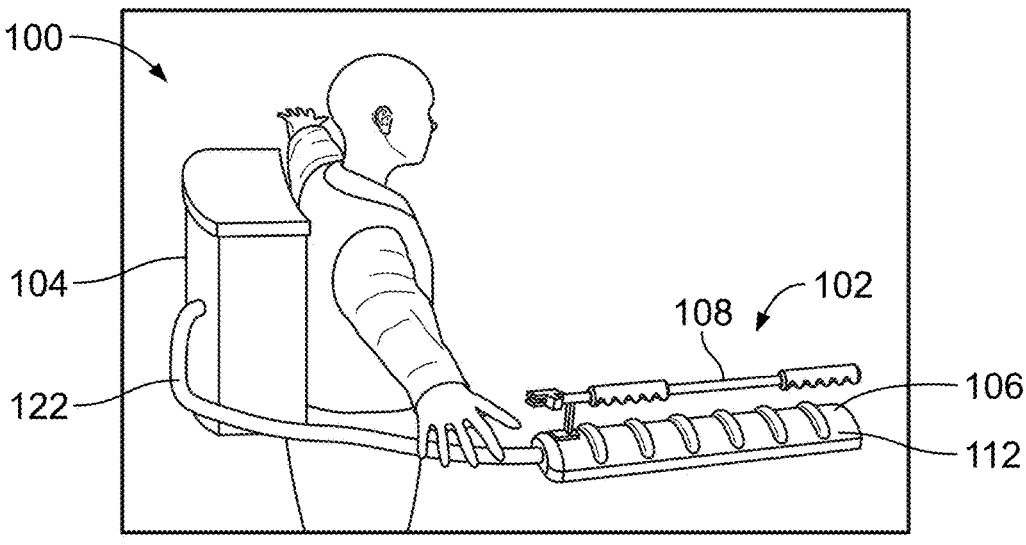
FIG. 5 illustrates a perspective view of the portable sanitizing system in a compact deployed position, according to an embodiment of the present disclosure.

FIG. 5 illustrates a perspective view of the portable sanitizing system 100 in a compact deployed position, according to an embodiment of the present disclosure. The wand assembly 102 is removed from the backpack assembly 104 (as shown in FIG. 1) into the compact deployed position, as shown in FIG. 5. The hose 122 connects the wand assembly 102 to the backpack assembly 104. In the compact deployed position, the sanitizing head 106 is fully retracted in relation to the handle 108.

Figure 6:
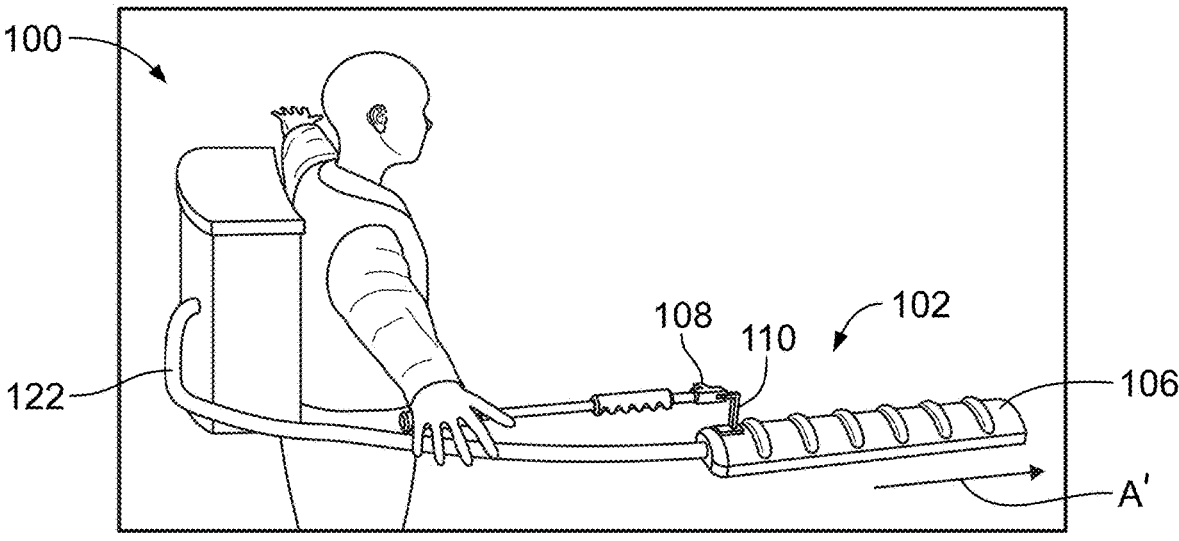
FIG. 6 illustrates a perspective view of the portable sanitizing system having a sanitizing head in an extended position, according to an embodiment of the present disclosure.

FIG. 6 illustrates a perspective view of the portable sanitizing system 100 having the sanitizing head 106 in an extended position, according to an embodiment of the present disclosure. In order to extend the sanitizing head 106 relative to the handle 108, the sanitizing head 106 is outwardly slid relative to the handle 108 in the direction of arrow A' (or the handle 108 is rearwardly slid relative to the sanitizing head 106). As noted, the sanitizing head 106 is able to linearly translate in the direction of arrow A' relative to the handle 108 via the coupler 110. The outward extension of the sanitizing head 106, as shown in FIG. 6, allows for the portable sanitizing system 100 to easily reach distant areas. Alternatively, the sanitizing head 106 may not linearly translate relative to the handle 108.

Figure 7:
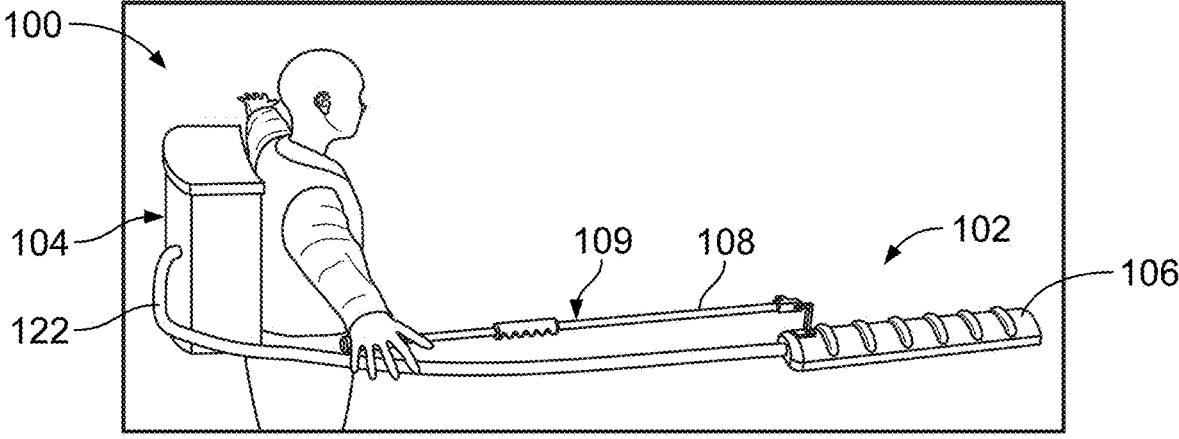
FIG. 7 illustrates a perspective view of the portable sanitizing system having the sanitizing head in an extended position and a handle in an extended position, according to an embodiment of the present disclosure.

FIG. 7 illustrates a perspective view of the portable sanitizing system 100 having the sanitizing head 106 in an extended position and the handle 108 in an extended position, according to an embodiment of the present disclosure. To reach even further, the handle 108 may be configured to linearly translate, such as through a telescoping portion, to allow the sanitizing head 106 to reach further outwardly. Alternatively, the handle 108 may not be configured to extend and retract.

In at least one embodiment, the handle 108 may include a lock 109. The lock 109 is configured to be selectively operated to secure the handle 108 into a desired extended (or retracted) position.

Figure 8:
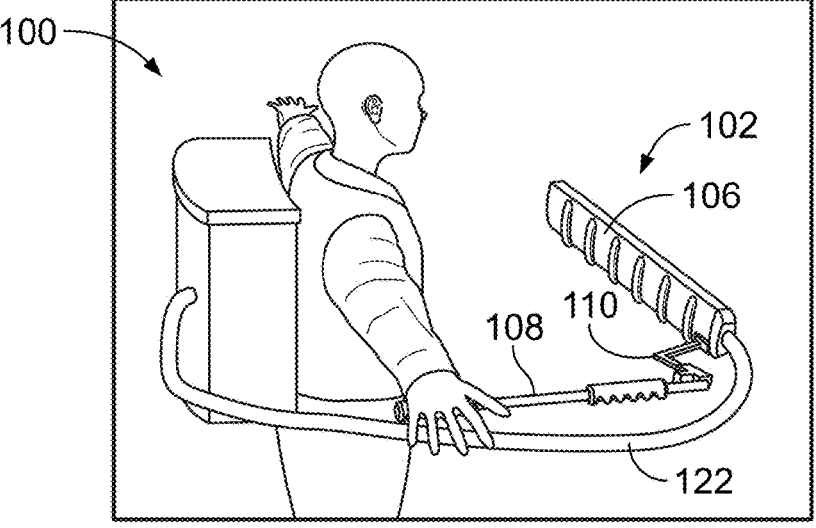
FIG. 8 illustrates a perspective view of the portable sanitizing system having the sanitizing head rotated in relation to the handle, according to an embodiment of the present disclosure.

FIG. 8 illustrates a perspective view of the portable sanitizing system 100 having the sanitizing head 106 rotated in relation to the handle 108, according to an embodiment of the present disclosure. As noted, the sanitizing head 106 is configured to rotate relative to the handle 108 via the coupler 110. Rotating the sanitizing head 106 relative to the handle 108 allows the sanitizing head 106 to be moved to a desired position, and sweep or otherwise reach into areas that would otherwise be difficult to reach if the sanitizing head 106 was rigidly fixed to the handle 108. Alternatively, the sanitizing head 106 may not be rotatable relative to the handle 108.

Figure 9:
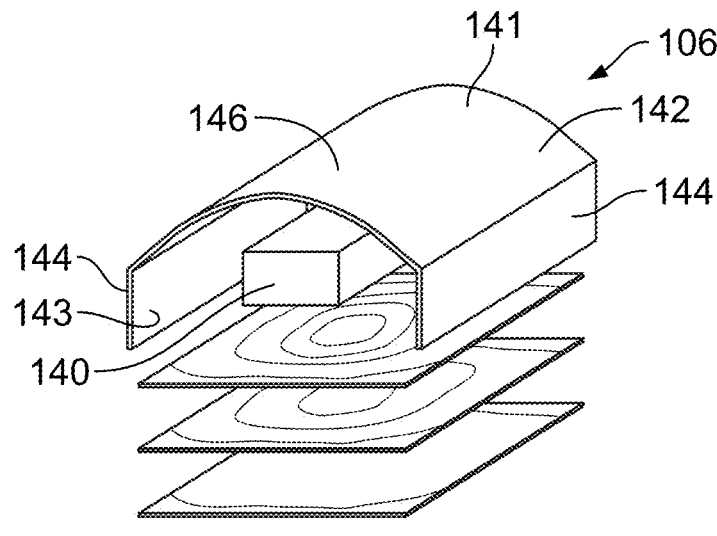
FIG. 9 illustrates a perspective end view of a UV lamp and a reflector of the sanitizing head, according to an embodiment of the present disclosure.

FIG. 9 illustrates a perspective end view of a UV lamp 140 and a reflector 142 of the sanitizing head 106, according to an embodiment of the present disclosure. The UV lamp 140 and the reflector 142 are secured within the shroud 112 (shown in FIG. 2, for example) of the sanitizing head 106. In at least one embodiment, the reflector 142 is secured to an underside 141 of the shroud 112, such as through one or more adhesives. As another example, the reflector 142 is an integral part of the shroud 112. For example, the reflector 142 may be or otherwise provide the underside 141 of the shroud 112. The reflector 142 provides a reflective surface 143 (such as formed of Teflon, a mirrored surface, and/or the like) that is configured to outwardly reflect UV light emitted by the UV lamp 140. In at least one example, shroud 112 may be or include a shell formed of fiberglass, and the reflector 142 may be formed of Teflon that provides a 98% reflectivity. In at least one embodiment, the reflector 142 may be a multi-piece reflector.

The reflector 142 may extend along an entire length of the underside 141 of the shroud 112. Optionally, the reflector 142 may extend along less than an entire length of the underside 141 of the shroud 112.

The UV lamp 140 may extend along an entire length (or along substantially the entire length, such as between the ends 116 and 118). The UV lamp 140 is secured to the reflector 142 and/or the shroud 112 through one or more mounts, such as brackets, for example. The UV lamp 140 includes one or more UV light emitters, such as one more bulbs, light emitting elements (such as light emitting diodes), and/or the like. In at least one embodiment, the UV lamp 140 is configured to emit UV light in the far UV spectrum, such as at a wavelength between 200 nm-230 nm. In at least one embodiment, the UV lamp 140 is configured to emit UV light having a wavelength of 222 nm. For example, the UV lamp 140 may be or include a 300 W bulb that is configured to emit UV light having a wavelength of 222 nm. Alternatively, the UV lamp 140 may be configured to emit UV light in other portions of the UV spectrum, such as the UVC spectrum. In at least one embodiment, the UV lamp 140 is configured to emit UV light having a wavelength of 254 nm.

As shown, the reflector 142 includes flat, upright side walls 144 connected together through an upper curved wall 146. The upper curved wall 146 may be bowed outwardly away from the UV lamp 140. For example, the upper curved wall 146 may have a parabolic cross-section and/or profile.

It has been found that the straight, linear side walls 144 provide desired reflection and/or focusing of UV light emitted from the UV lamp 140 toward and onto a desired location. Alternatively, the side walls 144 may not be linear and flat.

Figure 10:
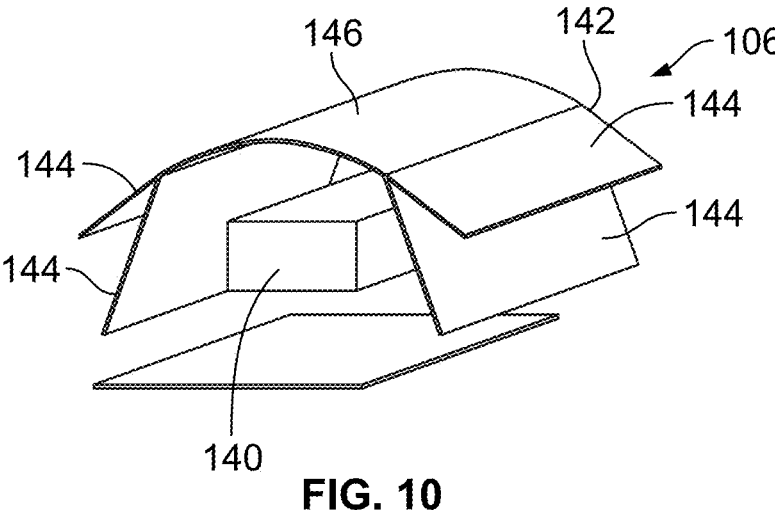
FIG. 10 illustrates a perspective end view of a UV lamp and a reflector of the sanitizing head, according to an embodiment of the present disclosure.

FIG. 10 illustrates a perspective end view of the UV lamp 140 and a reflector 142 of the sanitizing head, according to an embodiment of the present disclosure. The reflector 142 shown in FIG. 10 is similar to the reflector 142 shown in FIG. 9, except that the side walls 144 may outwardly cant from the upper curved wall 146.

Figure 11:
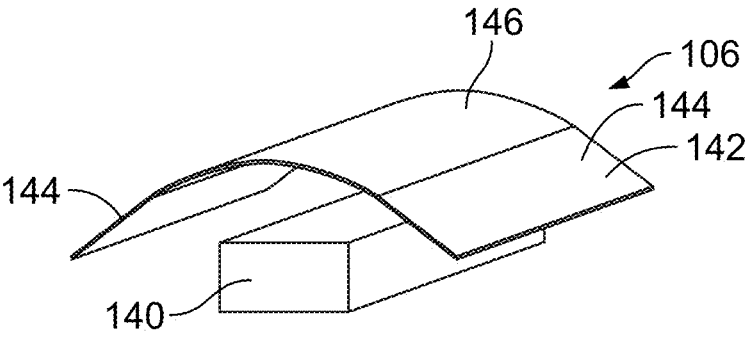
FIG. 11 illustrates a perspective end view of a UV lamp and a reflector of the sanitizing head, according to an embodiment of the present disclosure.

FIG. 11 illustrates a perspective end view of the UV lamp 140 and the reflector 142 of the sanitizing head, according to an embodiment of the present disclosure. In this embodiment, the side walls 144 may be curved according to the curvature of the upper curved wall 146.

Figure 12:
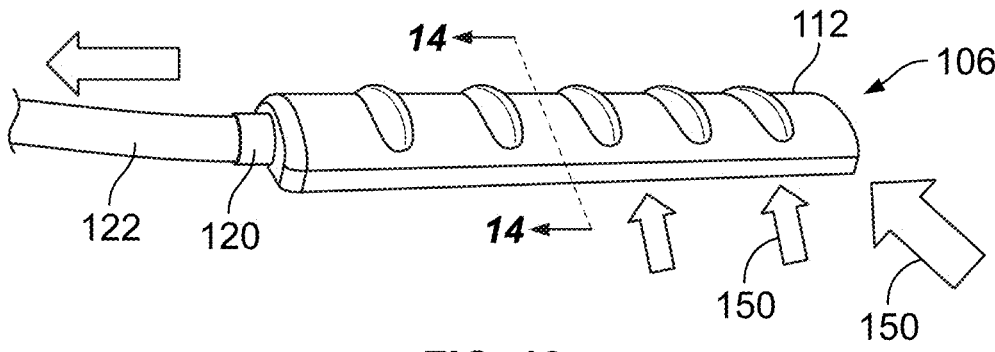
FIG. 12 illustrates a perspective top view of the sanitizing head.
Figure 13:
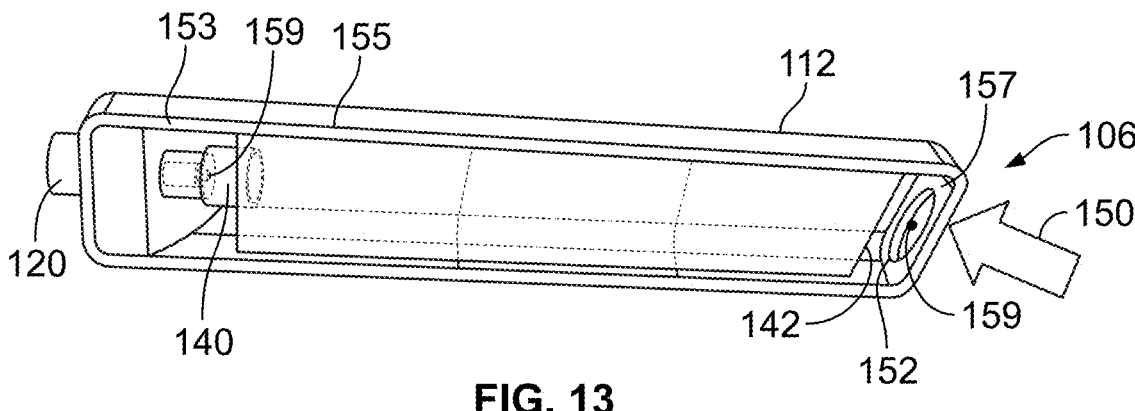
FIG. 13 illustrates a perspective bottom view of the sanitizing head.
Figure 14:
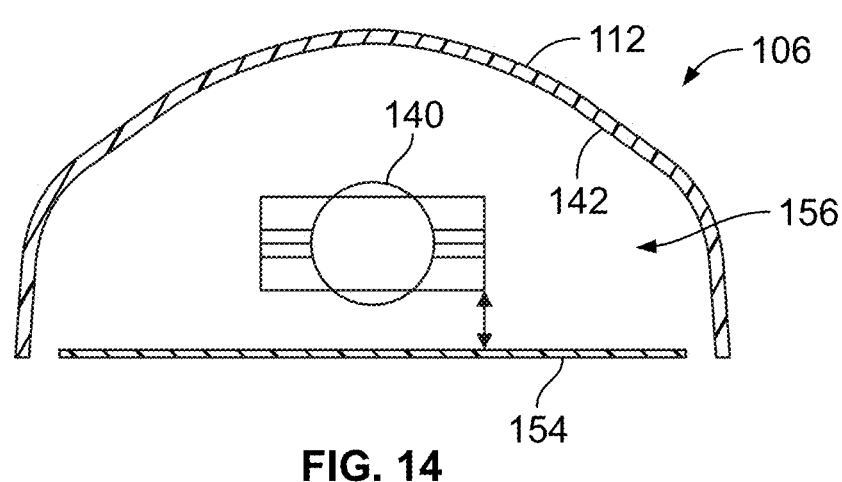
FIG. 14 illustrates an axial cross-sectional view of the sanitizing head through line 14-14 of FIG. 12.

FIG. 12 illustrates a perspective top view of the sanitizing head 106. FIG. 13 illustrates a perspective bottom view of the sanitizing head 106. FIG. 14 illustrates an axial cross-sectional view of the sanitizing head 106 through line 14-14 of FIG. 12. Referring to FIGS. 12-14, air 150 is configured to be drawn into the sanitizing head 106 through one or more openings 152 (or simply an open chamber) of the shroud 112. The air 150 is drawn into the sanitizing head 106, such as via a vacuum generator within the backpack assembly 104 (shown in FIG. 1). The air 150 is drawn into the shroud 112, and cools the UV lamp 140 as it passes over and around the UV lamp 140. The air 150 passes into the port 120 and into the hose 122, such as within an air tube within the hose 122. The air 150 not only cools the UV lamp 140, but also removes ozone, which may be generated by operation of the UV lamp 140, within the shroud 112. The air 150 may be drawn to an air filter, such as an activated carbon filter, within the backpack assembly 104.

In at least one embodiment, the portable sanitizing system 100 may also include an alternative ozone mitigation system. As an example, the ozone mitigation system may be disposed in the shroud 112 or another portion of the system, and may include an inert gas bath, or a face inert gas system, such as in U.S. Pat. No. 10,232,954.

Referring to FIG. 13, in particular, a bumper 153 may be secured to an exposed lower circumferential edge 155 of the shroud 112. The bumper 153 may be formed of a resilient material, such as rubber, another elastomeric material, open or closed cell foam, and/or the like. The bumper 153 protects the sanitizing head 106 from damage in case the sanitizing head 106 inadvertently contacts a surface. The bumper 153 also protects the surface from damage.

The openings 152 may be spaced around the lower surface of the shroud 112 such that they do not provide a direct view of the UV lamp 140. For example, the openings 152 may be positioned underneath portions that are spaced apart from the UV lamp 140.

Referring to FIG. 14, in particular, the sanitizing head 106 may include a cover plate 154 below the UV lamp 140. The cover plate 154 may be formed of glass, for example, and may be configured to filter UV light emitted by the UV lamp 140. The UV lamp 140 may be secured within an interior chamber 156 defined between the reflector 142 and the cover plate 154. In at least one embodiment, the cover plate 154 is or otherwise includes a far UV band pass filter. For example, the cover plate 154 may be a 222 nm band pass filter that filters UV light emitted by the UV lamp 140 to a 222 nm wavelength. As such, UV light that is emitted from the sanitizing head 106 may be emitted at a wavelength of 222 nm.

Referring to FIGS. 13 and 14, a rim 157 (such as a 0.020" thick Titanium rim) may connect the cover plate 154 to the shroud 112. The rim 157 may distribute impact loads therethrough and/or therearound.

In at least one embodiment, ranging light emitting diodes (LEDs) 159 may be disposed proximate to ends of the UV lamp 140. The ranging LEDs 159 may be used to determine a desired range to a structure that is to be sanitized, for example. In at least one embodiment, the ranging LEDs 159 may be disposed on or within the rim 157 and/or the cover plate 154. As another example, the sanitizing head 106 may be configured for range guidance, as disclosed in U.S. Provisional Application No. 63/027,869, which was filed May 20, 2020.

Figure 15:
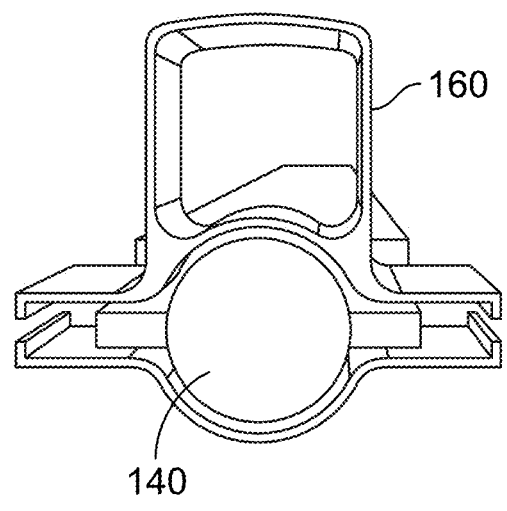
FIG. 15 illustrates a perspective end view of the UV lamp secured to a mounting bracket, according to an embodiment of the present disclosure.

FIG. 15 illustrates a perspective end view of the UV lamp 140 secured to a mounting bracket or clamp 160, according to an embodiment of the present disclosure. Each end of the UV lamp 140 may be coupled to mounting bracket or clamp 160, which secures the UV lamp 140 to the shroud 112 (shown in FIGS. 12-14). A buffer, such as a thin (for example, 0.040") sheet of silicon may be disposed between the end of the UV lamp 140 and the bracket 160. Optionally, the UV lamp 140 may be secured to the shroud 112 through brackets or clamps that differ in size and shape than shown.

As another example, the UV lamp 140 may be secured to the shroud 112 through adhesives, fasteners, and/or the like.

Figure 16:
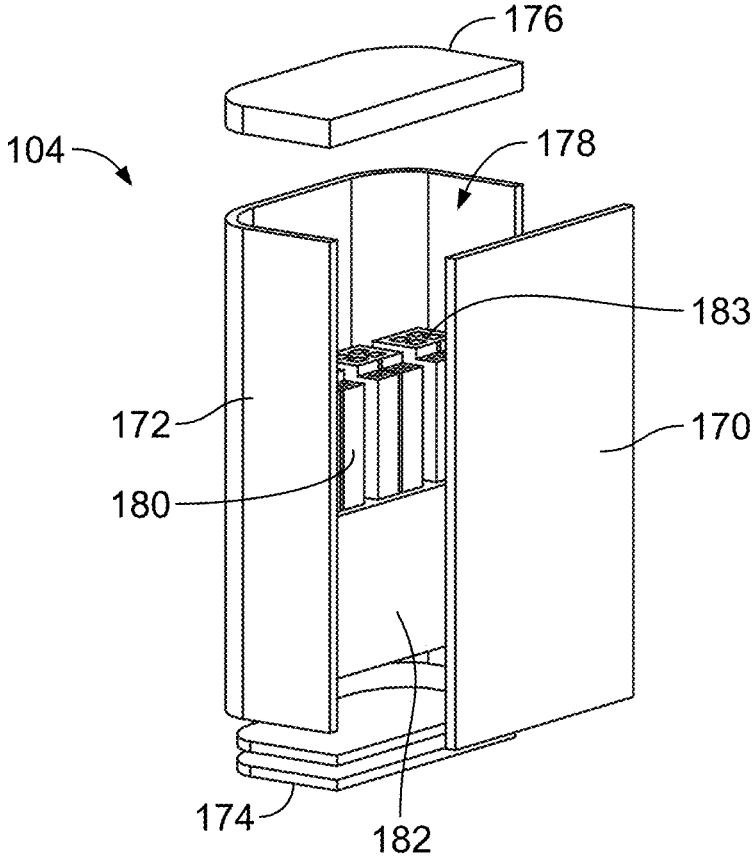
FIG. 16 illustrates a perspective exploded view of a backpack assembly, according to an embodiment of the present disclosure.

FIG. 16 illustrates a perspective exploded view of the backpack assembly 104, according to an embodiment of the present disclosure. The backpack assembly 104 includes a front wall 170 that couples to a rear shell 172, a base 174, and a top cap 176. An internal chamber 178 is defined between the front wall 170, the rear shell 172, the base 174, and the top cap 176. One or more batteries 180, such as rechargeable Lithium batteries, are contained within the internal chamber 178. An air generation sub-system 182 is also contained within the internal chamber 178. The air generation sub-system 182 is in fluid communication with an air tube within the hose 122 (shown in FIG. 2, for example). The air generation sub-system 182 may include an airflow device, such as a vacuum generator, an air blower, and/or the like. The airflow device is configured to generate airflow to cool the UV lamp, draw air from the sanitizing head 106 into the backpack assembly 104 and out through an exhaust, draw or otherwise remove generated ozone away from the shroud 112, and/or the like.

One or more air filters 183, such as carbon filters, are within the backpack assembly 104. The air filters 183 are in communication with the air tube or other such delivery duct or line that routes air through the hose 122 and into the backpack assembly 104. The air filters 183 are configured to filter the air that is drawn into the backpack assembly 104 from the shroud 112. For example, the air filters 183 may be configured to remove, deactivate, or otherwise neutralize ozone.

The batteries 180 and/or a power supply within the backpack assembly 104 provides operating power for the UV lamp 140 of the sanitizing head 106 (shown in FIG. 2, for example). The top wall 176 may be removably coupled to the front wall 170 and the rear shell 172. The top wall 176 may be removed to provide access to the batteries 180 (such as to remove and/or recharge the batteries), for example. Additional space may be provided within the backpack assembly 104 for storage of supplies, additional batteries, additional components, and/or the like. In at least one embodiment, the front wall 170, the rear shell 172, the base 174, and the top cap 176 may be formed of fiberglass epoxy.

Figure 17:
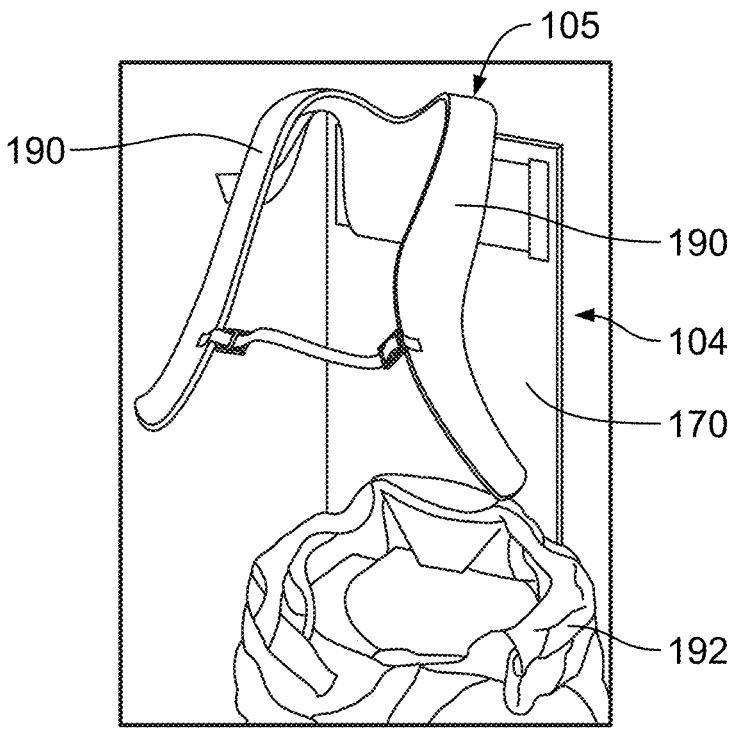
FIG. 17 illustrates a perspective front view of a harness coupled to a backpack assembly, according to an embodiment of the present disclosure.

FIG. 17 illustrates a perspective front view of the harness 105 coupled to the backpack assembly 104, according to an embodiment of the present disclosure. The harness 105 may include shoulder straps 190 and/or a waist or hip belt or strap 192, which allow the individual to comfortably wear the backpack assembly 104.

Referring to FIGS. 1-17, in operation, the individual may walk through an area wearing the backpack assembly 104. When a structure to be sanitized is found, the individual may position grasp the handle 108 and position the sanitizing head 106 as desired, such as by extending and/or rotating the sanitizing head 106 relative to the handle 108. The individual may then engage an activation button on the handle 108, for example, to activate the UV lamp 140 to emit sanitizing UV light onto the structure. As the UV lamp 140 is activated, air 150 is drawn into the shroud 112 to cool the UV lamp 140, and divert any generated ozone into the backpack assembly 104, where it is filtered by the air filters 183.

The extendable wand assembly 102 allows the sanitizing head 106 to reach distant areas, such as over an entire set of three passenger seats, from a row within an internal cabin of a commercial aircraft.

Figure 18:
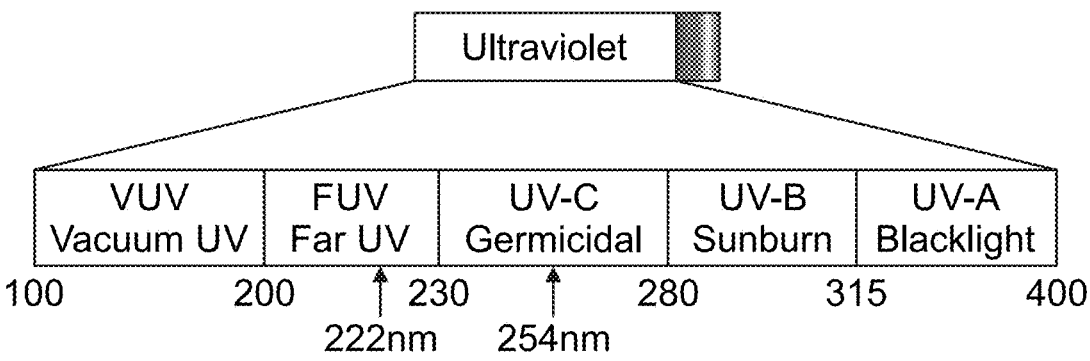
FIG. 18 illustrates an ultraviolet light spectrum.

FIG. 18 illustrates an ultraviolet light spectrum. Referring to FIGS. 1-18, in at least one embodiment, the sanitizing head 106 is configured to emit sanitizing UV light (through operation of the UV lamp 140) within a far UV spectrum, such as between 200 nm to 230 nm. In at least one embodiment, the sanitizing head 106 emits sanitizing UV light having a wavelength of 222 nm.

Figure 19:
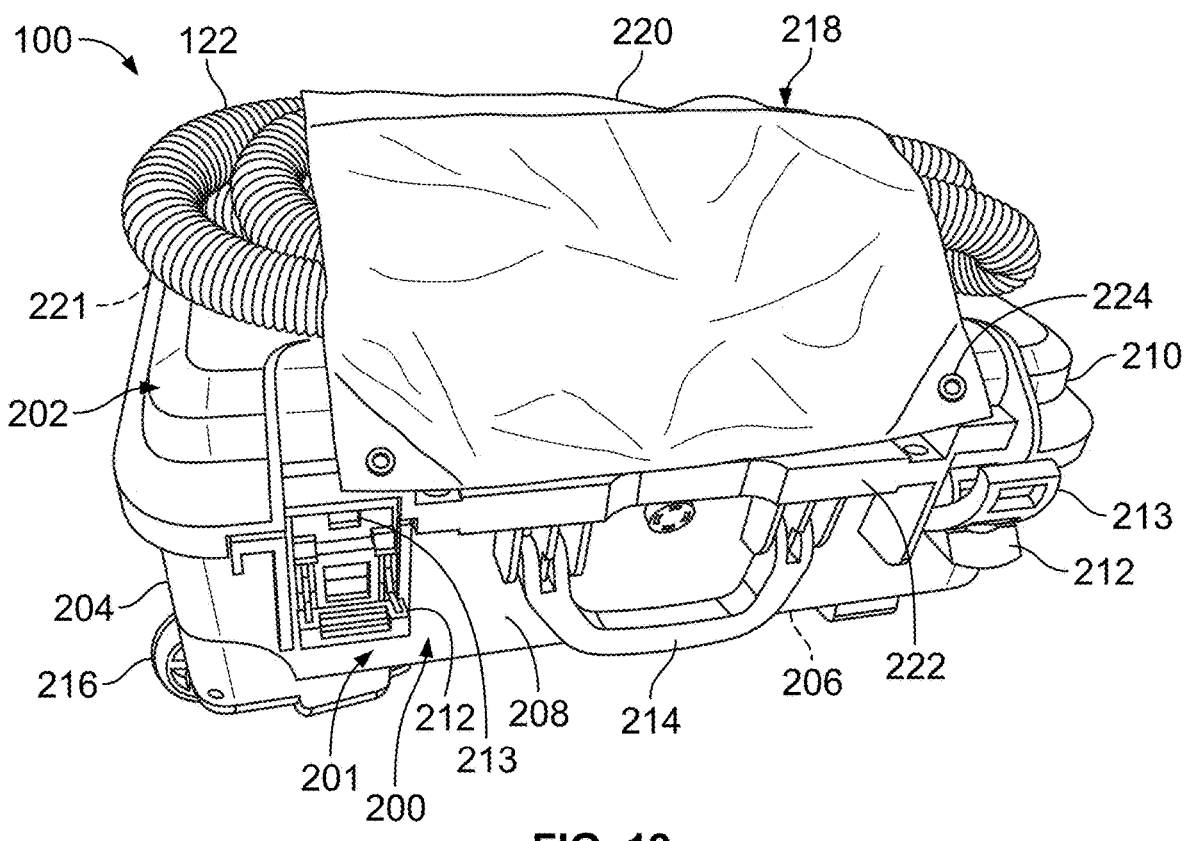
FIG. 19 illustrates a perspective view of a portable sanitizing system, according to an embodiment of the present disclosure.

FIG. 19 illustrates a perspective view of a portable sanitizing system 100, according to an embodiment of the present disclosure. The portable sanitizing system 100 includes a case assembly 200 that is configured to store the wand assembly 102 (hidden from view in FIG. 19) when the case assembly 200 is in a closed position, as shown in FIG. 19.

The case assembly 200 may be formed of plastic, for example. The case assembly 200 includes a main body 201, such as a shell, lower body portion, or the like. A cover 202, such as a lid, or upper body portion, is moveably coupled to the main body 201. For example, the cover 202 may be coupled to the main body 201 through a hinge that allows the cover 202 to be opened and closed relative to the main body 201.

The main body 201 includes a base 204 connected to a rear wall 206, lateral walls 208, and a top wall 210. The cover 202 is moveably coupled to a first lateral wall 208, such as through a hinge. One or more latches 212 are disposed on a second lateral wall 208, opposite from the first lateral wall 208. The latches 212 are configured to engage one or more reciprocal latch members 213 extending from the cover 202 to secure the cover 202 in the closed position. The latches 212 may be engaged by an individual to disengage the latch members 213 to allow the cover 202 to be pivoted into an open position.

A handle 214 is secured to the case assembly 200. For example, the handle 214 is pivotally secured to a lateral wall 208. The handle 214 is configured to be grasped by an individual so that the portable sanitizing system 100 may be carried. Optionally, the handle 214 may be secured to other portions of the case assembly 200, such as the top wall 210. In at least one embodiment, the handle 214 may be configured to retract into the case assembly 200 into a fully retracted position, and extend out of (for example, telescope out of) the case assembly 200 into a fully extended position.

Casters 216 or other such wheels may be rotatably secured to a portion of the case assembly 200. For example, two casters 216 may be rotatably secured to the base 204 proximate to the rear wall 206. An individual may tilt the case assembly 200 so that the casters 216 contact a floor. In this manner, the individual may roll the portable sanitizing system 100 via the casters 216 (and optionally through a handle in an extended position from the top wall 210). Alternatively, the case assembly 200 may not include the casters 216.

The hose 122 may outwardly extend from the case assembly 200. In the closed position, when the wand assembly 102 is in a stowed position within the case assembly 200, the hose 122 may be coiled over the cover 202. A hose retainer 218 may secure the hose 122 in place on the cover 202. For example, the hose retainer 218 may include a flexible fabric sheet 220 that is secured to a first side 221 of the cover 202, and may removably secured to an opposite second side 222 of the cover 202, such as through one or more fastening members 224, such as hooks and loops, latches, clips, and/or the like. The hose retainer 218 is configured to secure the hose 122 on the cover 202 when the wand assembly 102 is within a storage chamber of the case assembly 200 and the cover 202 is in a closed position. Alternatively, the hose 122 may be contained within a storage chamber of the case assembly 200 when the wand assembly 102 is not in use. That is, the storage chamber may be sized and shaped to also contain the hose 122 when the wand assembly 102 is also within the storage chamber and the cover 202 is in the closed position.

The wand assembly 102 within the case assembly 200 in the closed position is protected from inadvertent engagement, bumping, and the like. That is, by storing the wand assembly 102 within the case assembly 200, which is closed, when the wand assembly 102 is not in use, the portable sanitizing system 100 protects the wand assembly 102 from potential damage, and increases the useful life of the wand assembly 102.

Figure 20:
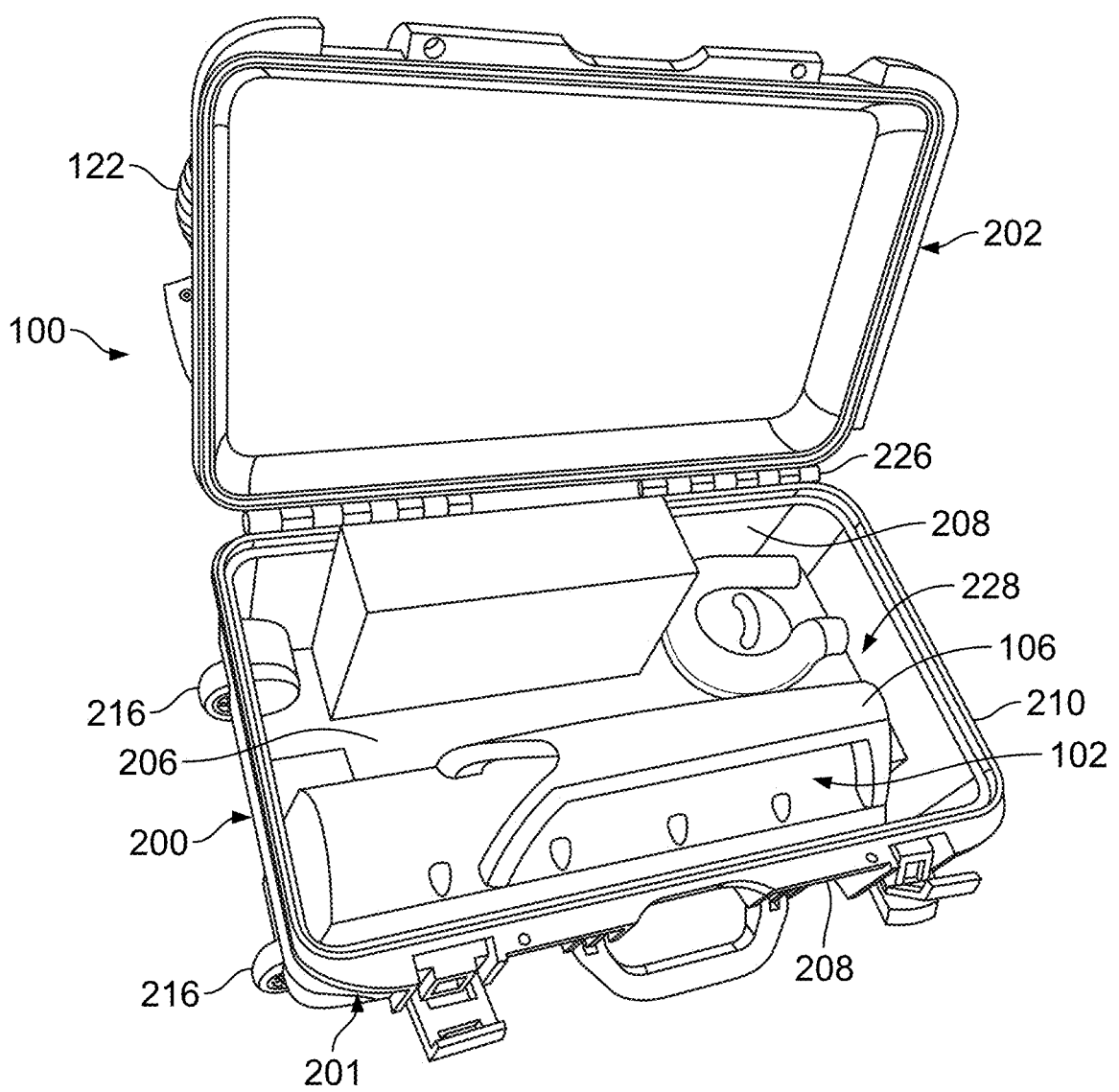
FIG. 20 illustrates a perspective view of the portable sanitizing system having a case assembly in an open position, according to an embodiment of the present disclosure.

FIG. 20 illustrates a perspective view of the portable sanitizing system 100 having the case assembly 200 in an open position, according to an embodiment of the present disclosure. As shown, the cover 202 is opened via a hinge 226 that pivotally couples the cover 202 to the main body 201.

An internal or storage chamber 228 is defined between the base 204, the lateral walls 208, the rear wall 206, and the top wall 210 (and the cover 202, when closed). Various components of the portable sanitizing system 100 may be stored within the storage chamber 228. For example, the components within the backpack assembly 104, as described with respect to FIG. 16, may be contained within the storage chamber 228.

For example, when not in use, the wand assembly 102 is contained within the storage chamber 228. Additionally, one or more batteries, such as rechargeable Lithium batteries, may be contained within the storage chamber 228.

An air generation sub-system (such as a cooling fan) may also be contained within the storage chamber 228. The air generation sub-system may be in fluid communication with an air tube within the hose 122. The hose 122 may be removably connected to the air generation sub-system. In at least one embodiment, the hose 122 is configured to be coupled to and uncoupled from the wand assembly 102 and the air generation sub-system. That is, the hose 122 may be removably coupled to the wand assembly 102 and the air generation sub-system.

One or more air filters, such as carbon filters, may also be within the storage chamber 228. The air filters may be in communication with the air tube or other such delivery duct or line that routes air through the hose 122.

Figure 21:
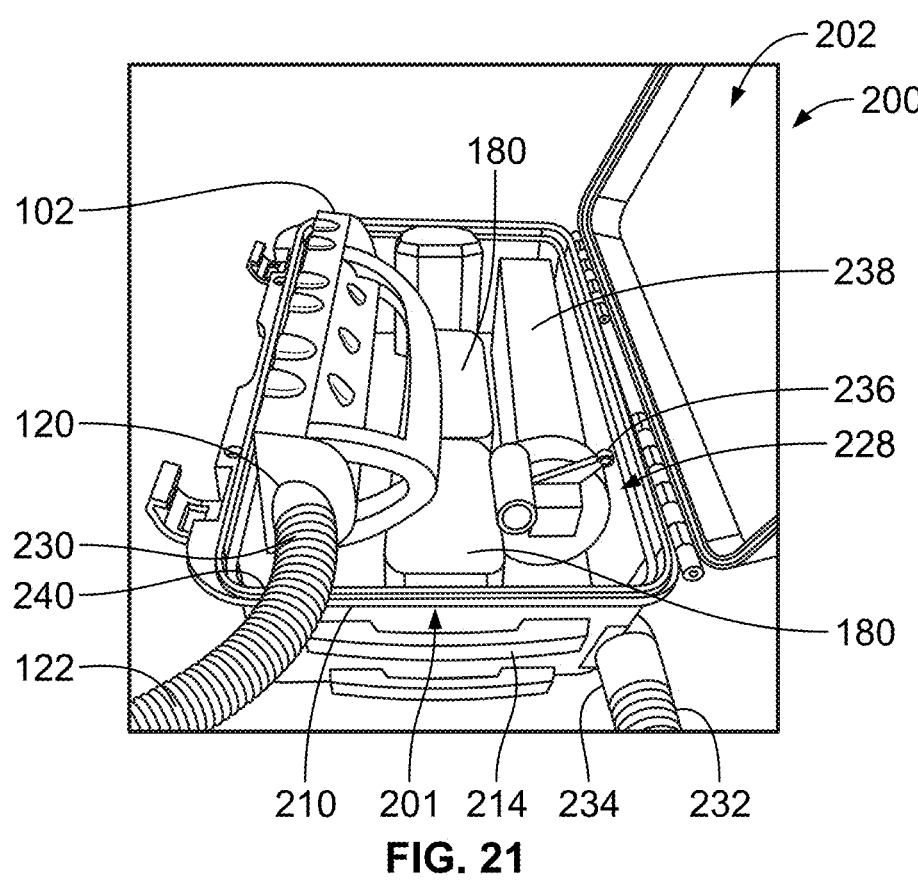
FIG. 21 illustrates a perspective view of the portable sanitizing system having the case assembly in the open position, according to an embodiment of the present disclosure.

FIG. 21 illustrates a perspective view of the portable sanitizing system 100 having the case assembly 200 in the open position, according to an embodiment of the present disclosure. The wand assembly 102 is configured to be stowed in the storage chamber 228. When the wand assembly 102 is to be used, the cover 202 is opened, and a first end 230 of the hose 122 is coupled to the port 120 of the wand assembly 102. In at least one embodiment, the hose 122 is configured to channel cooling air into the wand assembly 102, in order to cool the UV lamp 140 during activation.

A second end 232 of the hose 122 may be connected to a port 234 extending into and through a portion of the main body 201, such as through a portion of the top wall 210. The port 234 connects the hose 122 to an air generation sub-system, such as a cooling fan 236 that is within the storage chamber 228. The cooling fan 236 may be activated to generate cooling air that is delivered to the wand assembly 102 through the hose 122 (such as an air tube within the hose 122, or through an internal passage of the hose 122 itself).

One or more batteries 180 may also be stowed within the storage chamber 228. For example, three batteries 180 may be within the storage chamber 228.

A power supply 238 is also contained within the storage chamber 228. The power supply 238 may be coupled to the wand assembly 102 through a power cord (such as via a plug and receptacle fitting) to provide power to the wand assembly 102. Further, the power supply 238 may be configured to provide power to the batteries 180 (such as to recharge the batteries 180). The batteries 180 may be secured to the wand assembly 102 and provide power to the wand assembly 102, so that the wand assembly 102 may be used without connection to the power supply 238.

The cooling fan 236 couples to the hose 122 via the port 234. The cooling fan 236 may also include a diverter port that couples to an internal portion of the power supply 238. In this manner, cooling air may be delivered to both the hose 122 (and therefore the wand assembly 102), and the power supply 238, thereby providing cooling to both the wand assembly 102 and the power supply 238.

A hole 240 may be formed through a portion of the case assembly 200. For example, a hole 240 may be formed through a portion of the top wall 210 and sized and shaped to allow the hose 122 to pass therethrough. In this manner, the hose 122 may remain connected to the wand assembly 102 even when the wand assembly 102 is contained within the storage chamber 228 and the cover 202 is closed. Other portions of the hose 122 between the first end 230 and the second end 232 may be secured to the cover 202 by the hose retainer 218, as shown and described with respect to FIG. 19.

As shown, the handle 214 may be secured to the top wall 210 of the main body 201. The handle 214 may be configured to retracted into and extend out of the main body 201. For example, the handle 214 may be a telescoping handle.

The wand assembly 102 is removably secured within the storage chamber 228. For example, the wand assembly 102 may be removably secured within the storage chamber 228 by one or more latches, clips, or via an interference fir with a conforming portion of the case assembly 200.

The power supply 238 may be fixed in position within the storage chamber 228. For example, the power supply 238 may be fixed in the storage chamber 228 by one or more fasteners, adhesives, or the like. Optionally, the power supply 238 may be secured in position by one or more latches, clips, or the like.

The batteries 180 may similarly be fixed position within the storage chamber 228. For example, the batteries 180 may be fixed in the storage chamber 228 by one or more fasteners, adhesives, or the like. Optionally, the batteries 180 may be secured in position by one or more latches, clips, or the like. In at least one other embodiment, the batteries 180 may be removable, and configured to couple directly to the wand assembly 102 to provide power thereto.

Figure 22:
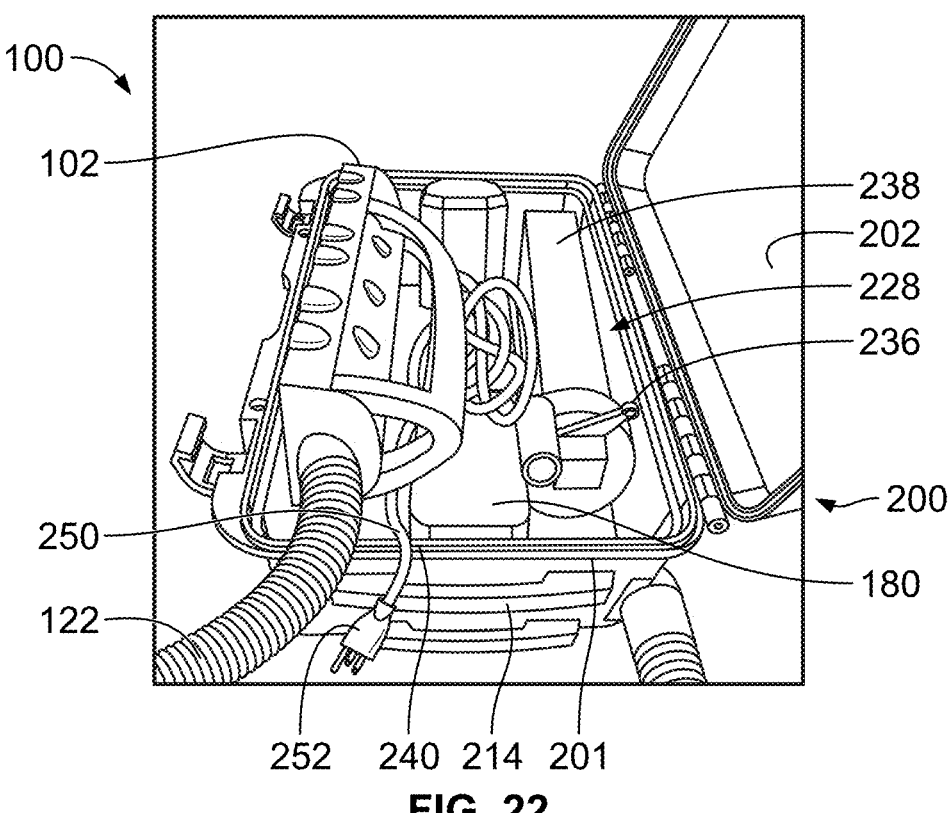
FIG. 22 illustrates a perspective view of the portable sanitizing system having the case assembly in the open position, according to an embodiment of the present disclosure.

FIG. 22 illustrates a perspective view of the portable sanitizing system 100 having the case assembly 200 in the open position, according to an embodiment of the present disclosure. A power cord 250 may also be stowed within the storage chamber 228. The power cord 250 is contained within the case assembly 200 when the cover 202 is closed and the portable sanitizing system 100 is moved when the wand assembly 102 is not being operated.

Optionally, the power cord 250 connects the power supply 238 to a source of power (such as a wall outlet). In addition to supply air to the wand assembly 102, the hose 122 also routes electrical cables and the like to the wand assembly 102 from the power supply 238 and the batteries 180.

Optionally, the hose 122 may not include electrical connections to the wand assembly 102. Instead, the wand assembly 102, the power cord 250 may plug into the wand assembly 102, via the plug 252, to supply power from the power supply 238 and/or the batteries 180. In this embodiment, as the wand assembly 102 is operated, the plug 252 of the power cord 250 is connected to a reciprocal receptacle of the wand assembly 102. An opposite end of the power cord 250 is connected to the power supply 238 (and/or, a battery 180). The power cord 250 extends out of the case assembly 200 through the hole 240. Thus, the wand assembly 102 may be removed from the storage chamber 228 and connected to the hose 122 and the power cord 250, which extend through the hole 240. The cover 202 may then be closed, thereby securely retaining the power supply 238, the batteries 180, and the like within the storage chamber 228. The wand assembly 102 may then be activated, as it is powered via the power supply 238 or one or more of the batteries 180, and the closed case assembly 200 may be moved, such as via an individual grasping the handle 214 and rolling the case assembly 200 via the casters 216 (shown in FIGS. 19 and 20).

Further, the hole 240 also allows intake air to be drawn into the storage chamber 228, even when the cover 202 is closed over the main body 201. Accordingly, the cooling fan 236 is able to receive fresh air, even when the cover 202 is closed.

The power supply 238 may be configured to receive power from a standard power supply, such as a source of alternating current power. For example, the power supply 238 may connect to the source of alternating current power through a power cord. The power cord 250 connects to the wand assembly 102, and is configured to deliver power to the wand assembly 102 to operate the UV lamp 140 from power received from the power supply 238 and optionally the batteries 180. For example, when the power supply 238 is connected to a source of alternating current power, the wand assembly 102 is powered by the power supply 238. In the absence of such power, the wand assembly 102 may be powered by the batteries 180. For example, the wand assembly 102 receives power from the batteries 180 the power supply 238 is not plugged into a power outlet. If the power supply 238 is plugged into a power outlet, one or more relays in the power supply 238 switch over from the batteries 180 to alternating current power supply from the power outlet.

Figure 23:
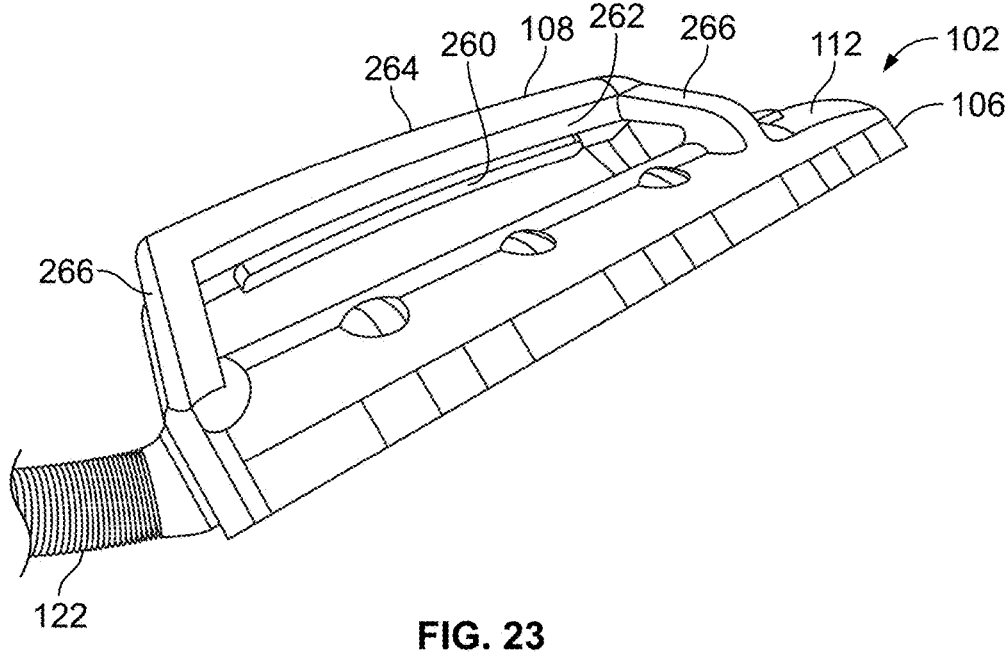
FIG. 23 illustrates a perspective lateral view of the wand assembly, according to an embodiment of the present disclosure.

FIG. 23 illustrates a perspective lateral view of the wand assembly 102, according to an embodiment of the present disclosure. As shown, the handle 108 may be fixed in relation to the shroud 112. For example, the handle 108 may be integrally molded and formed with the shroud 112. The wand assembly 102 may be small and compact in order to fit in confined spaced, such as within a flight deck of an aircraft.

An activation trigger 260 is moveably coupled to the handle 108. For example, the activation trigger 260 may be secured to an underside 262 of a main beam 264 of the handle 108. The activation trigger 260 is configured to be selectively pressed and/or depressed to activate and deactivate the UV lamp 140 of the wand assembly 102, as desired.

The activation trigger 260 may be located anywhere along the length of the handle 108. The activation trigger 260 may be shaped differently than shown. Further, the activation trigger 260 may be smaller or larger than shown. As an example, the activation trigger 260 may be a circular button, instead of an elongated bar or beam, as shown. Also, optionally, the activation trigger 260 may be located on a top portion of the main beam 264, or on an extension beam 266, which spaces the handle 108 from the shroud 112. As another example, the activation trigger 260 may be located on a portion of the shroud 112.

Figure 24:
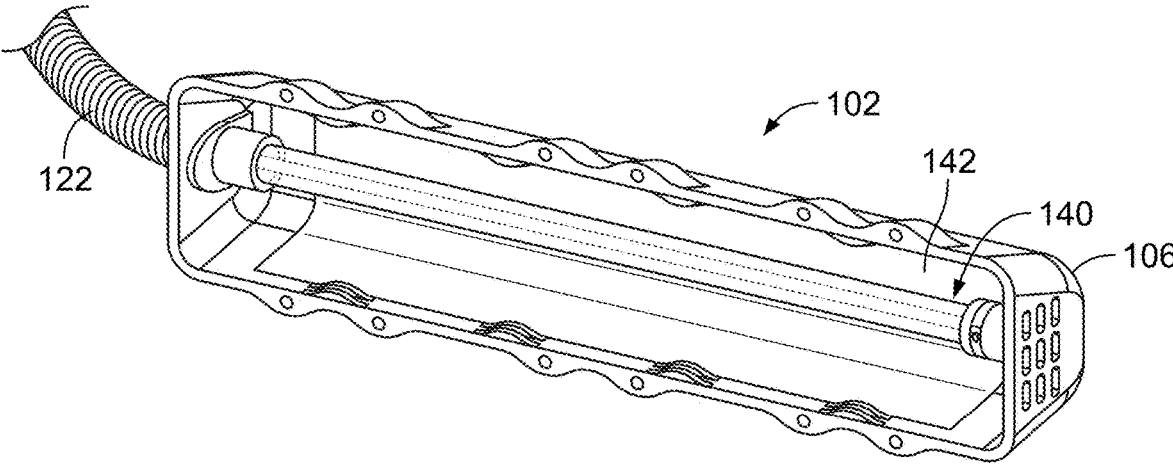
FIG. 24 illustrates a perspective bottom view of the wand assembly of FIG. 23.

FIG. 24 illustrates a perspective bottom view of the wand assembly 102 of FIG. 23. As shown, the reflector 142 is secured to an underside of the shroud 112.

Figure 25:
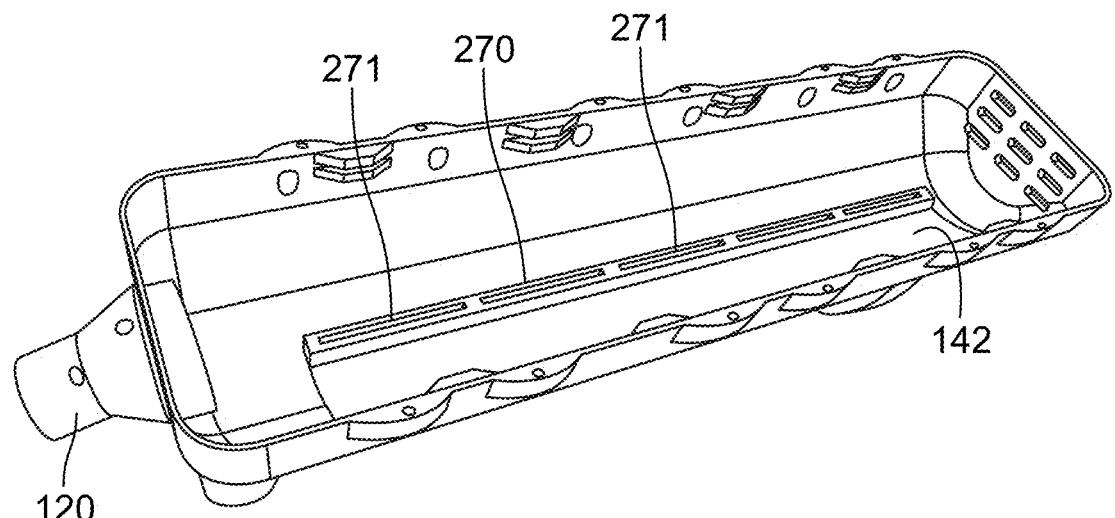
FIG. 25 illustrates a perspective bottom view of the wand assembly of FIGS. 23 and 24 without the UV lamp, according to an embodiment of the present disclosure.
Figure 26:
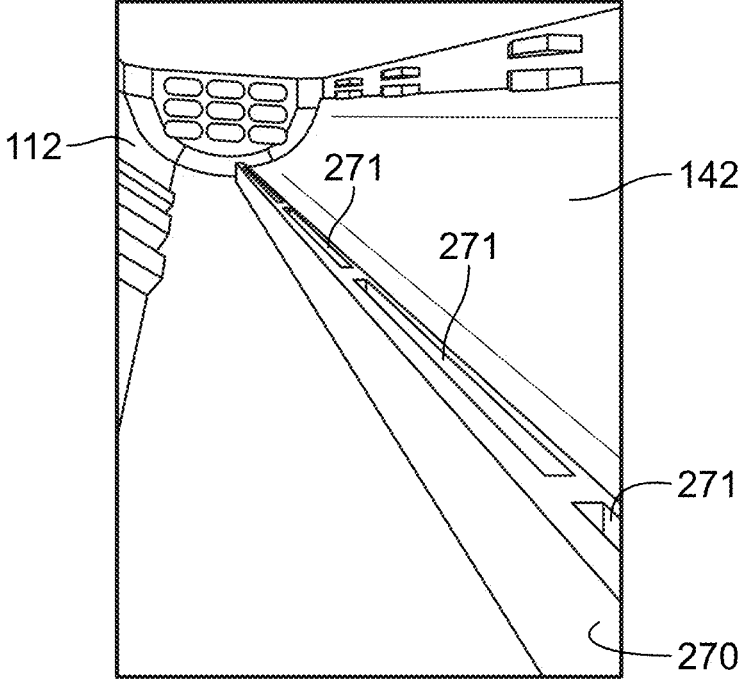
FIG. 26 illustrates a perspective view of a cooling manifold of a shroud of the wand assembly, according to an embodiment of the present disclosure.

FIG. 25 illustrates a perspective bottom view of the wand assembly 102 of FIGS. 23 and 24 without the UV lamp 140 (for the sake of clarity), according to an embodiment of the present disclosure. FIG. 26 illustrates a perspective view of a cooling manifold 270 of the shroud 112 of the wand assembly 102. Referring to FIGS. 25 and 26, a half of the reflector 142 is removed to expose a cooling manifold 270 that extends through the shroud 112 and is in fluid communication with the port 120. The cooling manifold 270 has a plurality of air outlets 271 that allow air delivered through the hose 122 (shown in FIG. 23, for example) that is coupled to the port 120 to pass over the UV lamp 140 when activated. In this manner, the UV lamp 140 is cooled during operation. The delivered air passes over and around the reflector 142 (which is disposed between the cooling manifold 270 and the UV lamp 140), through a channel defined through the reflector 142, and/or between two portions of the reflector 142 (such as a first half of the reflector 142 and a second half of the reflector 142).

Referring to FIGS. 19-26, the portable sanitizing system 100 includes the wand assembly 102 including the sanitizing head 106 having the UV lamp 140. The case assembly 200 includes the cover 202 coupled to the main body 201. The cover 202 is configured to be moved between an open position that exposes the storage chamber 228 and a closed position. The wand assembly 102 is configured to be stored in the storage chamber 228 when not in use and removed from the storage chamber 228 to disinfect one or more components with UV light emitted by the UV lamp 140.

In at least one embodiment, the portable sanitizing system 100 includes the wand assembly 102 and the case assembly 200, which may be a rolling case assembly. The wand assembly 102 includes the UV lamp 140. The cooling manifold 270 is configured to allow air to blow across the UV lamp 140, such as one or more bulbs of the UV lamp 140. The wand assembly 102 may also include a two piece reflector 142, a master power switch, and a trigger switch, such as the activation trigger 260, to activate and illuminate the UV lamp 140.

During use of the wand assembly 102, the case assembly 200 may be placed away from the area being disinfected, thereby allowing the operator to transport only the wand assembly 102 to the area, and facilitating movement and operation in tight or confined spaces. The wand assembly 102 may include a 300 watt, 222 nm UV lamp, optional ranging lights, the cooling manifold 270 running the length of the shroud 112, the reflector 142, mounts (such as brackets, clamps, fasteners, and/or the like) to secure the UV lamp 140 to the shroud 112, a master power switch on the handle 108, and the activation trigger 260 on the handle 108 that is configured to be engaged to selectively activate and deactivate the UV lamp 140. The reflector 142 may be made out of Teflon or an aluminum sheet, which allows the reflector 142 to provide electromagnetic shielding. The UV lamp 140 may be attached to the shroud 112 with wire straps or bands, which may be positioned on top of Teflon tape and dry woven fiberglass that serve as a cushion between the strap and the glass bulb.

Figure 27:
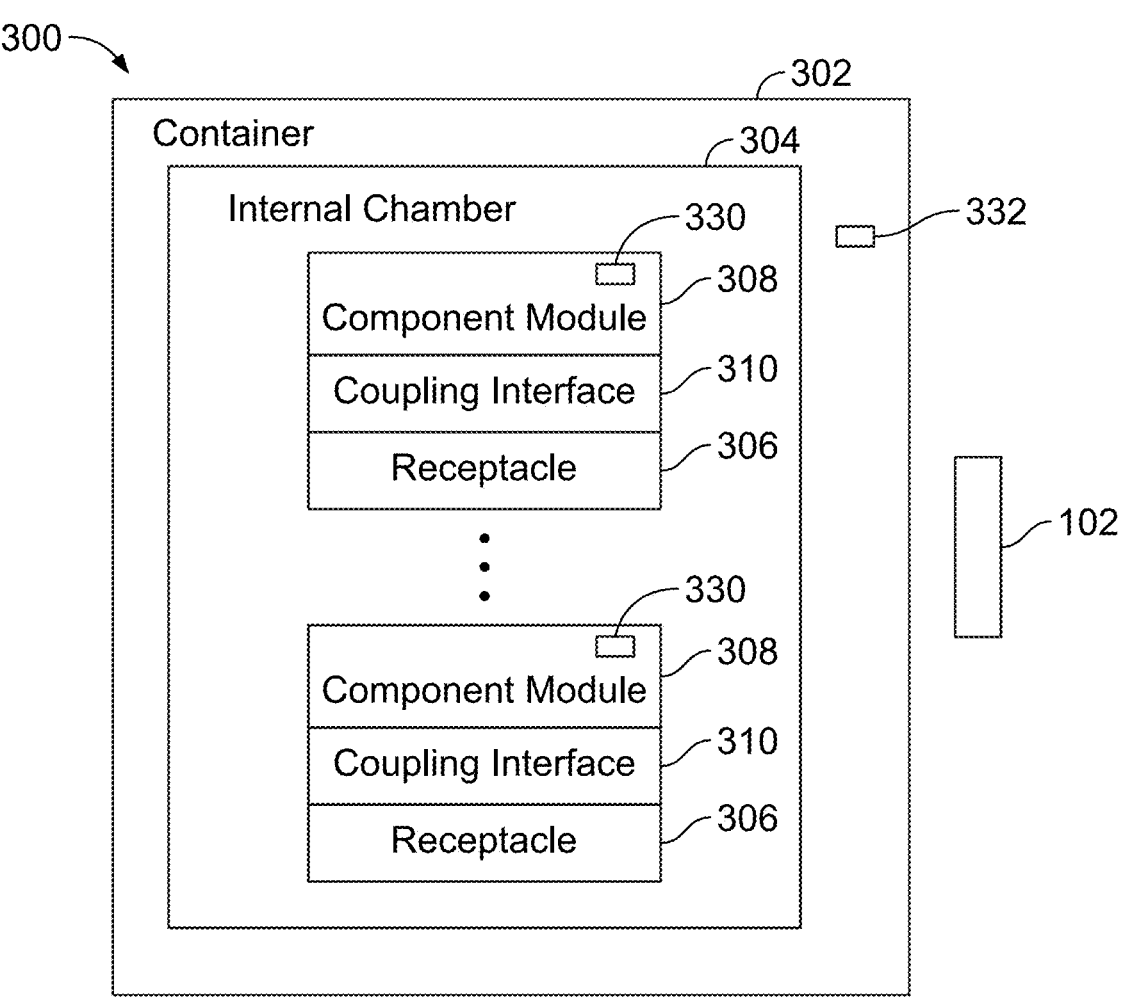
FIG. 27 illustrates a schematic block diagram of a portable sanitizing system, according to an embodiment of the present disclosure.

FIG. 27 illustrates a schematic block diagram of a portable sanitizing system 300, according to an embodiment of the present disclosure. The portable sanitizing system 300 includes a container 302 that defines or otherwise includes an internal chamber 304. The backpack assembly 104 shown in FIGS. 1, 5-8, and 16-17 is an example of the container 302. The case assembly 200 shown in FIGS. 19-22 is another example of the container 302. A cart assembly, such as shown and described in U.S. patent application Ser. No. 17/026,435, entitled "Ultraviolet Light Sanitizing Cart," filed Sep. 21, 2020, is another example of the container 302.

The internal chamber 304 includes a plurality of receptacles 306 or other such mounting locations that are configured to receive and removably retain a plurality of component modules 308. Examples of the component modules 308 includes a power supply, a battery pack, a blower or fan, a wand assembly, and/or the like, as described herein. The internal chamber 304 can include any number of receptacle 306, each of which is configured to removably retain a respective component module 308.

A wand assembly 102 is coupled to the container 302. The wand assembly 102 can be any of the wand assemblies described herein. The wand assembly 102 can be stowed within the internal chamber 304, and removed therefrom to sanitize surfaces with UV light, as described herein. In at least one embodiment, the wand assembly 102 is a component module 308 that is removably coupled to a receptacle 306 within the internal chamber 304.

The component modules 308 secure to the receptacles 306 at respective coupling interfaces 310. The component modules 308 are configured to be secured to, and removed from, the receptacles 306 at the coupling interfaces 310, such as without the use of tools. The component modules 308 are removably secured to the container 302, such as with respect the receptacles 306. The component modules 308 are removably secured to the container 302 in that they are configured to be selectively and repeatedly secured to and removed from the container 302, such as without the use of tools. As an example, the coupling interfaces 310 include fasteners that are configured to be manipulated by hand, such as quarter turn wing-style fasteners. As another example, the coupling interfaces 310 include plug and socket connections. As another example, the coupling interfaces 310 include latches. As another example, the coupling interfaces 310 includes deflectable detents. As another example, the coupling interface 310 include snaps. As another example, the coupling interfaces 310 include mechanical and electrical couplings, such as plugs and sockets.

The component modules 308 are configured to be removably secured within the container 302, such as via the coupling interfaces 310. As such, the component modules 308 can be quickly and easily removed, repaired outside of the container 302, and/or replaced with another component module. Further, the component modules 308 can be removed from a first container, such as of a case assembly, a backpack assembly, or a cart assembly, and inserted into a second container that differs from the first container, such as another one of a case assembly, a backpack assembly, or a cart assembly The component modules 308 can be interchangeable with respect to the receptacles 306 within the container 302. The coupling interfaces 310 can be the same for each of the component modules 308 and the receptacles 306. For example, the coupling interfaces 310 can be standardized to provide a common securing connection for all of the component modules 308. As such, a first component module 308 within the container 302 can be removed from a first receptacle 306, and moved to a second receptacle 306 within the container 302. Additionally, component modules 308 can be interchanged within the container 302 and/or another container with different component modules 308.

In at least one other embodiment, the sanitizing system may not be portable. Instead, the sanitizing system can be fixed in a location, such as within a galley, lavatory, or the like of a vehicle. The fixed sanitizing system can include the container 302.

FIG. 28 illustrates a simplified view of a coupling interface 310 between a component module 308 and a receptacle 306, according to an embodiment of the present disclosure. As shown, the coupling interface 310 includes a plug 312 that mates with a reciprocal socket 314 of the receptacle 306. When mated together, the plug 312 and the socket 314 provide a mechanical connection that secures the component module 308 to the receptacle 306. Further, the plug 312 and the socket 314 may also include electrical elements that provide an electrical connection between the component module 308 and the receptacle 306 when the plug 312 is mated with the socket 314. Optionally, the receptacle 306 can include the plug 312, and the component module 308 can include the receptacle 314.

FIG. 29 illustrates a simplified view of a coupling interface 310 between a component module 308 and a receptacle 306, according to an embodiment of the present disclosure. As shown, the coupling interface 310 includes one or more latches 316 of the receptacle 306 that are configured to latchably engage one or more strikes 318, of the component module 308. Optionally, the receptacle 306 can include the strike(s) 318, and the component module 308 can include the latch(es) 316.

FIG. 30 illustrates a simplified view of a coupling interface 310 between a component module 308 and a receptacle 306, according to an embodiment of the present disclosure. As shown, the coupling interface 310 includes one or more detents 320 (such as deflectable arms, spring-biased devices, or the like) of the receptacle 306 that are configured to deflect, and mate with one or more reciprocal members 322 (such as recesses, ledges, ridges, or the like) of the component module 308. Optionally, the receptacle 306 can include the reciprocal member(s) 322 and the component module 308 can include the detent(s) 320.

FIG. 31 illustrates a simplified view of a coupling interface between a component module and a receptacle, according to an embodiment of the present disclosure. As shown, the coupling interface 310 includes one or more snaps 324 of the receptacle 306 that are configured to snapably secured into one or more reciprocal recesses 326 of the component module 308. Optionally, the receptacle 306 can include the recess(es) 326 and the component module 308 can include the snap(s) 324.

FIGS. 28-31 show examples of coupling interfaces 310. Various other types of coupling interfaces 310 that allow the component modules 308 to be removably secured to the receptacles 306 can be used.

Referring to FIGS. 27-31, the component modules 308 of the portable sanitizing system 300 are configured for quick and easy removal and replacement. Spare component modules 308 can be stored to ensure that replacements can be quickly accomplished in the field, to maintain operational schedules. The component modules 308, including replacement component modules, can include radio frequency identification (RFID) tags 330. The RFID rags 330 allow the component modules 308 to be tracked and monitored. As such, inventory can be efficiently managed, the number of component modules 308 can be optimized for efficiency and cost benefits. Optionally, the component modules 308 may not include RFID tags.

The component modules 308 are secured to the container 302 via the coupling interfaces 310, such as may include quick-release fasteners and quick-release electrical connectors, which require little or no tools to secure and remove the component modules 308. In at least one embodiment, the portable sanitizing system 300 can be tracked and monitored via a global positioning system (GPS) device 332, using a GPS-enabled asset management system. The asset management system can provide asset status (battery state, remote diagnostics, etc.) and geographic location wirelessly to a control center and/or a remote computing device (such as handheld smart phone, smart tablet, personal or laptop computer, or the like). As such, efficiency can be improved by ensuring the portable sanitizing system 300 is fully functional when and where needed. Optionally, the container 302 may not include the GPS device.

Figure 32:
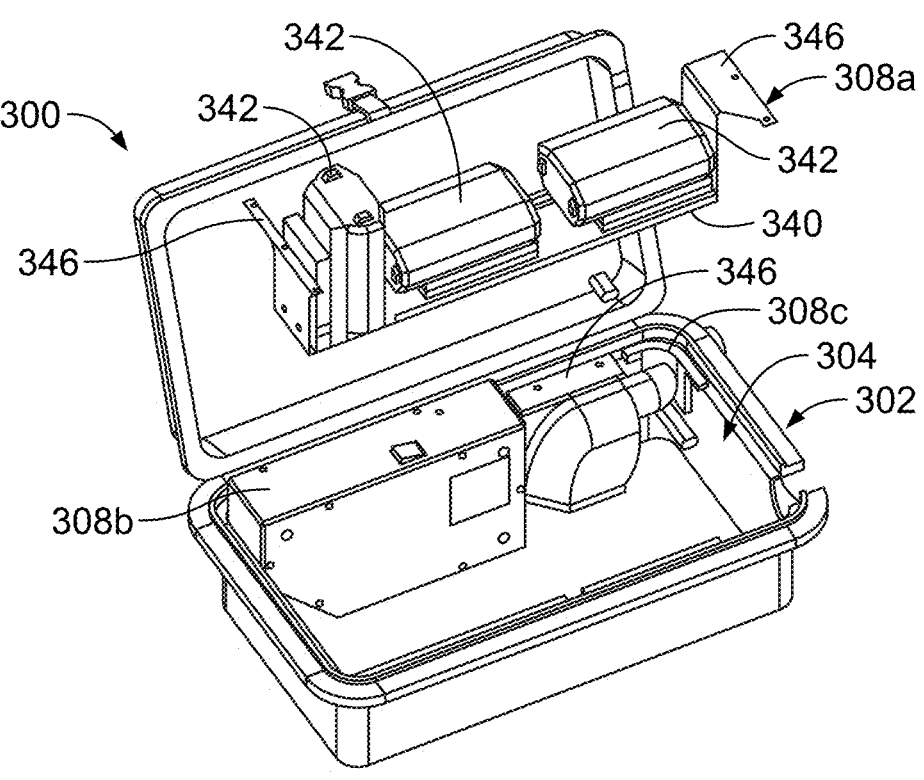
FIG. 32 illustrates a perspective view of a portable sanitizing system, according to an embodiment of the present disclosure.
Figure 33:
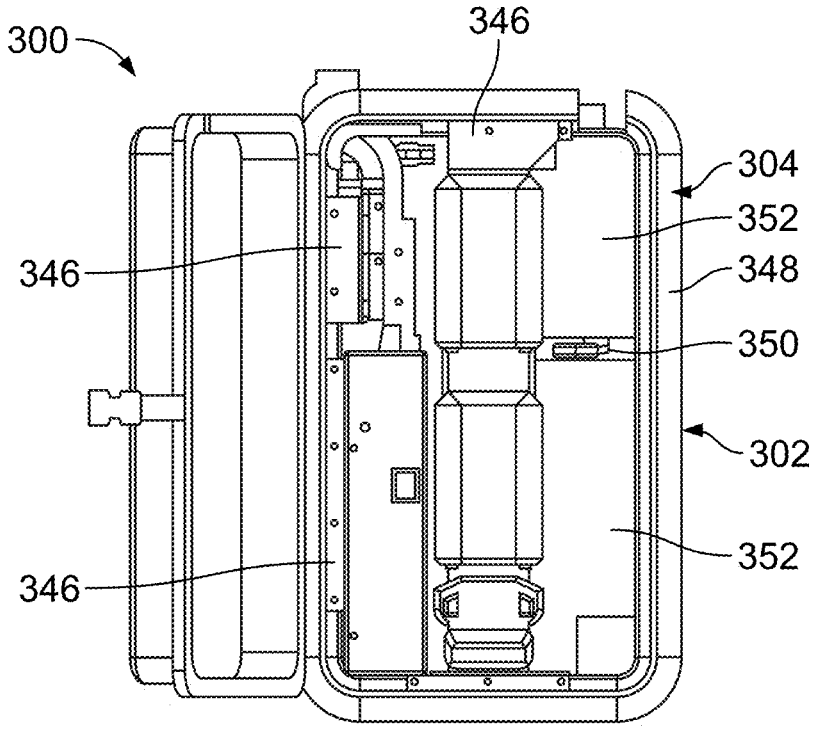
FIG. 33 illustrates a top view of the portable sanitizing system of FIG. 32.

FIG. 32 illustrates a perspective view of the portable sanitizing system 300, according to an embodiment of the present disclosure. FIG. 33 illustrates a top view of the portable sanitizing system 300 of FIG. 32. Referring to FIGS. 32 and 33, as shown, the container 302 is a case assembly. The component modules include a battery pack 308a, a power supply 308b, and a blower 308c. The battery pack 308a includes a support tray 340 that securely retains one or more batteries 342. The battery pack 308a can include more or less batteries 342 than shown.

As an example, the batteries 342 provide direct current (DC) power, such as 120 V DC power. The power supply 308b uses 110 alternating current (AC) power, such as may be provided from a main power source within a vehicle, building, or the like. For example, the power supply 308b can connect to the main power source through an electrical cord and plug. In at least one embodiment, the power supply 308b converts power from the main power source and/or the batteries 342 to a high voltage, high frequency power, such as 3000-5000 V at a frequency of 120 kHz.

As shown, the battery pack 308a, the power supply 308b, and the blower 308c include coupling interfaces that include flanges 346 that seat over portions of a ledge 348 of the container 302. The flanges 346 secure to the ledge 348 such as through any of the coupling interfaces described with respect to FIGS. 27-31. For example, quarter turn, hand engageable fasteners can be used to secure the flanges 346 to the ledge 348.

Additionally, a coupling interface 350 can be used to quickly connect and disconnect the batteries 342 in relation to the power supply 308b. The coupling interface 350 can be a plug/socket electrical connector, for example.

Additionally, the container 302 can include a bed 352 configured to support a wand assembly. The bed 352 can be formed of foam, for example.

Figure 34:
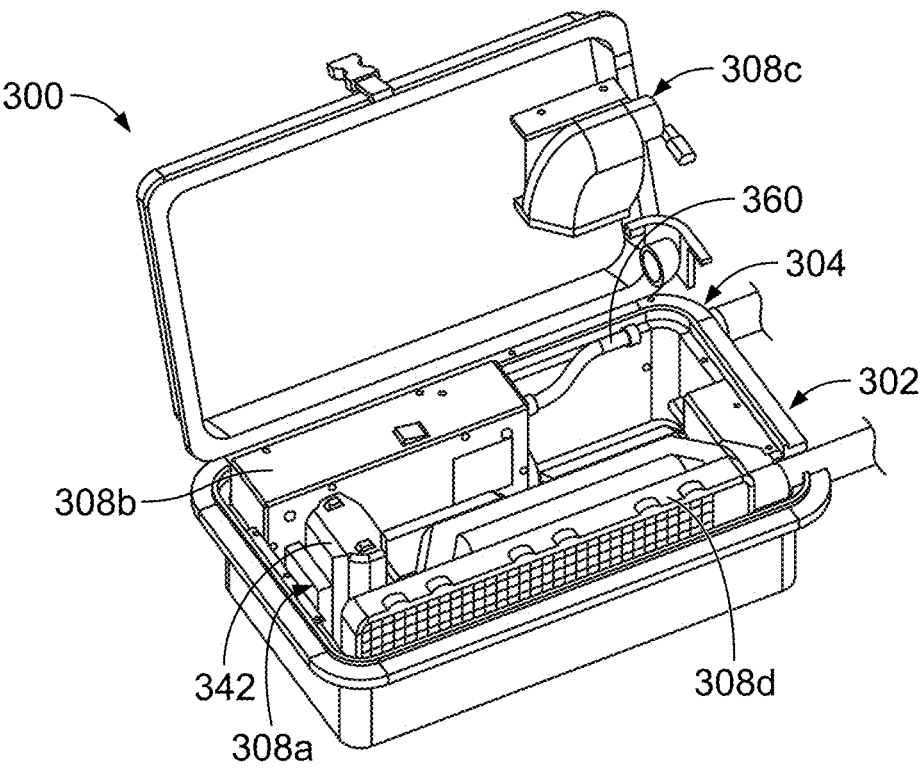
FIG. 34 illustrates a perspective view of a portable sanitizing system, according to an embodiment of the present disclosure.
Figure 35:
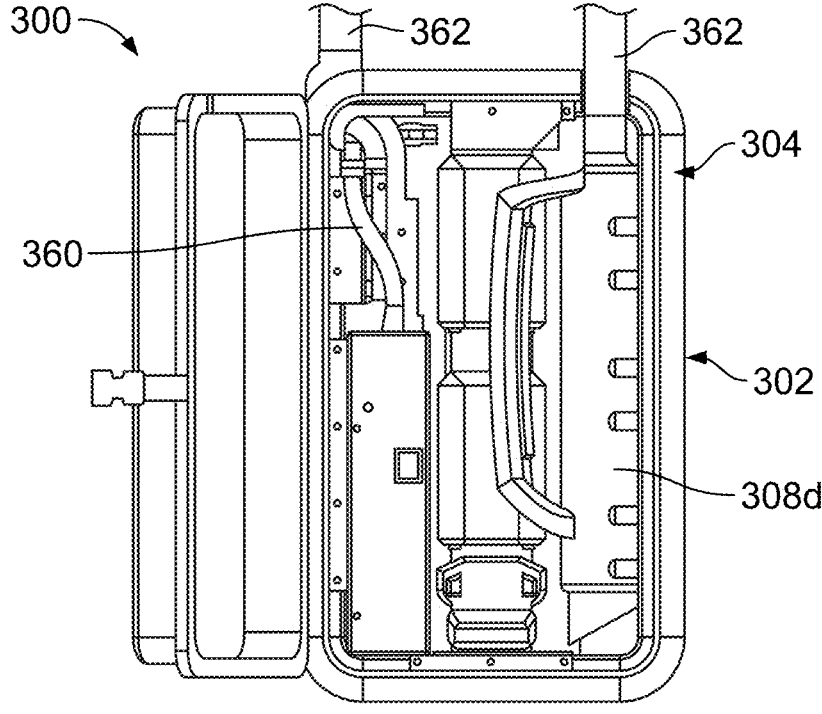
FIG. 35 illustrates a top view of the portable sanitizing system of FIG. 34.

FIG. 34 illustrates a perspective view of the portable sanitizing system 300, according to an embodiment of the present disclosure. FIG. 35 illustrates a top view of the portable sanitizing system 300 of FIG. 34. An electrical connector 360 extends from the power supply 308b, and is configured to removably connect to a wand assembly 308d through a reciprocal mating interface extending through a hose 362 that connects to the wand assembly 308d. The electrical connector 360 can also removably connect to the blower 308c through a reciprocal mating interface on and/or within the blower 308c.

Referring to FIGS. 32-35, the various component modules, such as the battery pack 308a, the power supply 308b, the blower 308c, and/or the wand assembly 308d can be secured within the container 302 and removed therefrom, as described with respect to FIGS. 27-35.

Figure 36:
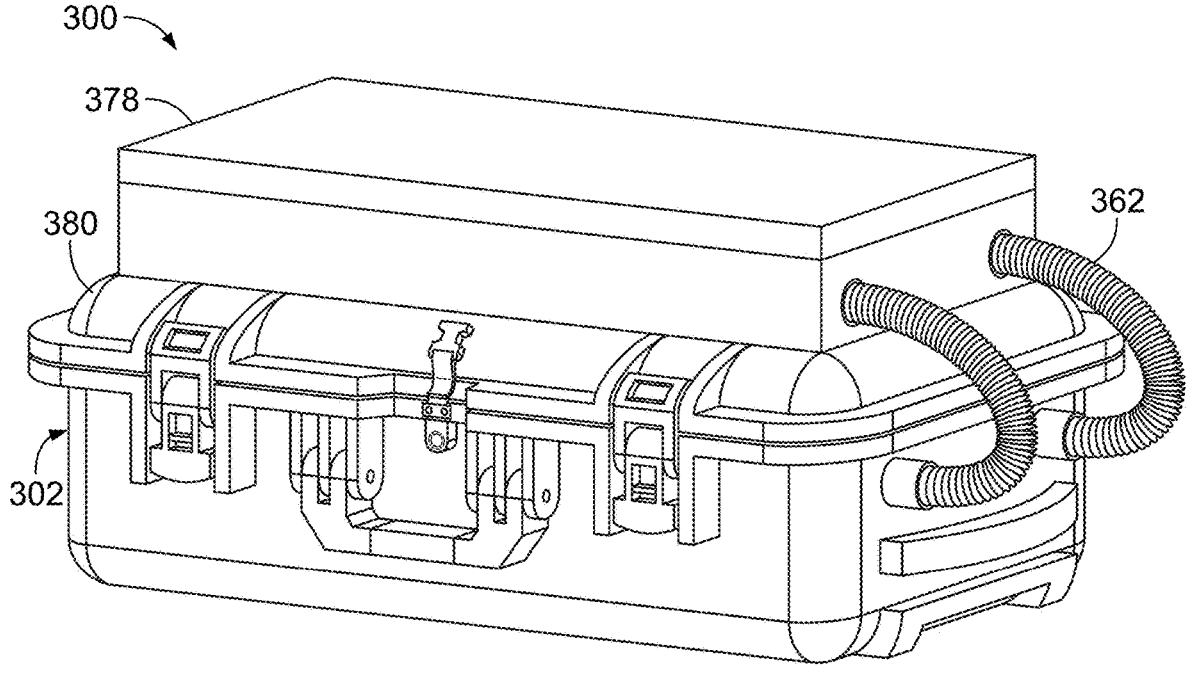
FIG. 36 illustrates a perspective side of a portable sanitizing system, according to an embodiment of the present disclosure.

FIG. 36 illustrates a perspective side of a portable sanitizing system 300, according to an embodiment of the present disclosure. In at least one embodiment, a retaining frame 378 can extend outwardly from a cover 380 of the container 302. The retaining frame 378 is configured to house supplemental or replacement component modules, such as additional battery packs. Additionally, portions of the hose 362 can be secured within or underneath the retaining frame 378 such as when the portable sanitizing system 300 is stowed away.

Figure 37:
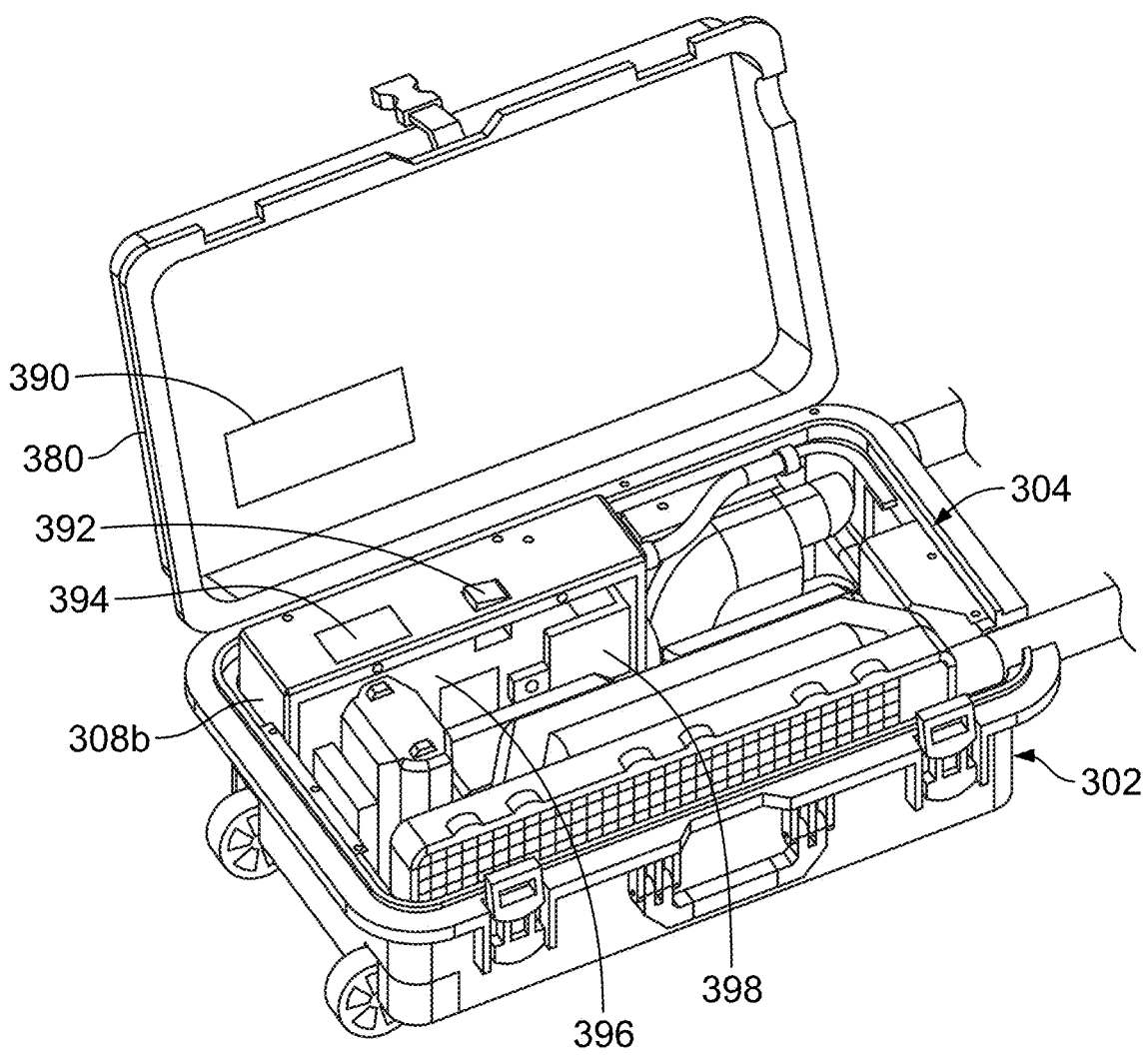
FIG. 37 illustrates a perspective top view of a portable sanitizing system, according to an embodiment of the present disclosure.

FIG. 37 illustrates a perspective top view of a portable sanitizing system 300, according to an embodiment of the present disclosure. In at least one embodiment, a window 390 is disposed within the cover 380. The window 390 can be an opening formed through the cover 380. As another example, the window 390 can be a transparent material disposed within, or formed as a portion of, the cover 380. For example, the window 390 can be formed of glass, a clear polycarbonate material, or the like. The window 390 is configured to provide a clear view into a portion of the internal chamber 304 when the cover 380 is closed, for example.

For example, the power supply 308b can include an activation switch 392 that illuminates when the power supply 308b is activated. An information screen 394 can also be disposed on the power supply 308b. The information screen 394 can be an electric monitor, such as including a liquid crystal display, light emitting diodes (LEDs), and/or the like that provide various status indicators for the portable sanitizing system 300. The status indicators can include an activation status, a power level, diagnostic information, such as battery life remaining, UV lamp temperature and status, and/or the like.

The window 390 is positioned to be over the activation switch 392 and the information screen 394 when the cover 380 is closed. As such, the window 390 allows an individual to view the activation switch 392 and the information screen 394 when the cover 380 is closed.

In at least one embodiment, a printed circuit board 396 can also be disposed within the internal chamber 304. For example, the printed circuit board 396 can be secured on and/or proximate to the power supply 308b. The printed circuit board 396 includes a microcontroller 398. In at least one embodiment, the printed circuit board 396 is, or is part of, a component module.

In at least one embodiment, the microcontroller 398 is configured to detect information regarding the component modules. For example, the microcontroller 398 detects a make and model of attached component modules, such as the wand assembly 308d, the battery pack 308a, the power supply 308b, the blower 308d, and/or the like. The microcontroller 398 is in communication with the various component modules, such as through one or more wired or wireless connections, when the component modules are plugged into the container 302, for example.

In at least one embodiment, the microcontroller 398 detects information regarding the a component module (such as make and model), based on a connector pin arrangement of the component module. The microcontroller 398 compares installed pin arraignment data to known (such as stored in memory) arrangements to determine compatibility of the component module. The microcontroller 398 outputs data signals that include messages, which may be displayed on the information screen 394. The messages are displayed on the information screen 394 in response to the pin arrangement comparison, for example. In at least one embodiment, the microcontroller 398 can further adjust system parameters, such as power level, to optimize the portable sanitizing system 300 with respect to particular component modules secured to the container 302. Optionally, the portable sanitizing system 300 may not include the window 390, the information screen 394, the printed circuit board 396, or the microcontroller 398.

Figure 38:
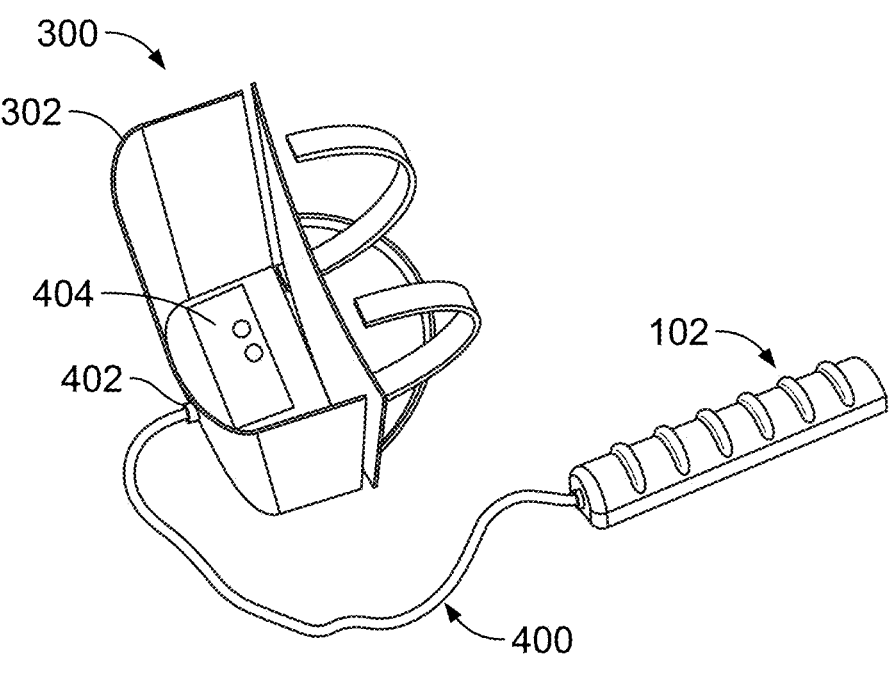
FIG. 38 illustrates a perspective lateral view of a portable sanitizing system, according to an embodiment of the present disclosure.

FIG. 38 illustrates a perspective lateral view of a portable sanitizing system 300, according to an embodiment of the present disclosure. As shown, the container 302 can be a backpack assembly. Optionally, the container 302 can be a case assembly, a cart assembly, or the like.

The wand assembly 102 can be a component module. The wand assembly 102 connects to a hose 400, which includes electrical wiring. The hose 400 can also include a fluid duct, such as an air tube. A first connector 402 is disposed at an end of the hose 400 opposite from the wand assembly 102. The first connector 402 is configured to removably connect to a second connector 404 on the container 302. As such, the first connector 402 and the second connector 404 provide a coupling interface.

The first connector 402 mates with the second connector 404 to provide a mechanical and electrical connection between the hose 400 (and therefore the wand assembly 102) and the container 302. The wand assembly 102 can be quickly and easily connected to and disconnected from the container 302 via the coupling interface between the first connector 402 and the second connector 404.

Figure 39:
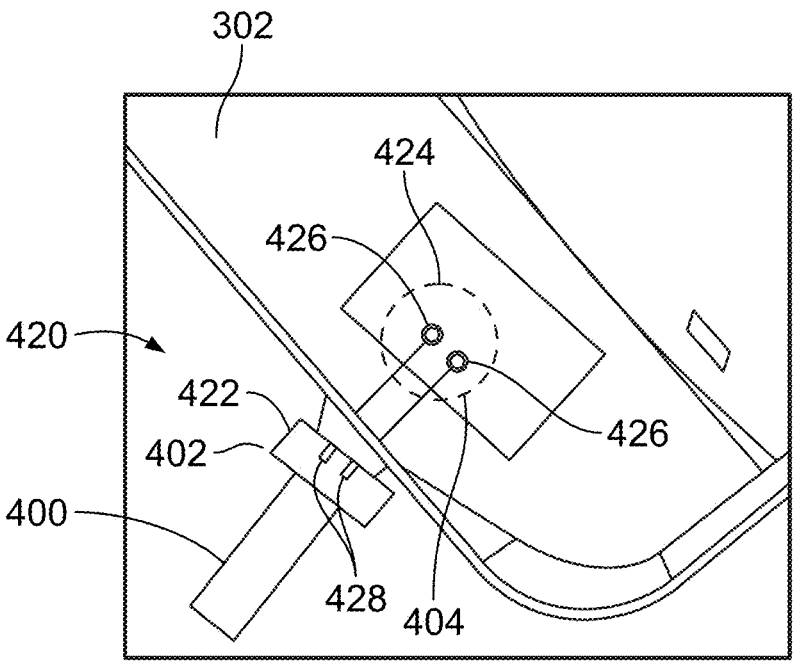
FIG. 39 illustrates a simplified view of a coupling interface between a hose and a container, according to an embodiment of the present disclosure.

FIG. 39 illustrates a simplified view of a coupling interface 420 between the hose 400 and the container 302, according to an embodiment of the present disclosure. The first connector 402 includes a threaded retainer 422 that threadably secures to a reciprocal member 424 of the second connector 404. The second connector 404 also includes one or more conductive receivers 426 that receive one or more conductive rods 428 of the first connector 402, such as through a slip fit. The threaded retainer 422 is threaded around the reciprocal member 424 to securely and safely mate the rods 428 with the receivers 426. Thus, the threaded hose retainer 422 can be rotated to selectively connect and disconnect the first connector 402 from the second connector 404.

In order to secure the hose 400 to the container 302, the threaded retainer 422 is aligned with the reciprocal member 424 so that the rods 428 are aligned with the receivers 426. The hose 400 is then urged toward the reciprocal member 424 so that the rods 428 are inserted into the receivers 426. The threaded retainer 422 is then rotated in relation to the reciprocal member in a securing direction to threadably secure the first connector 402 to the second connector 404. In order to remove the hose 400 from the container 302, the process is reversed.

Figure 40:
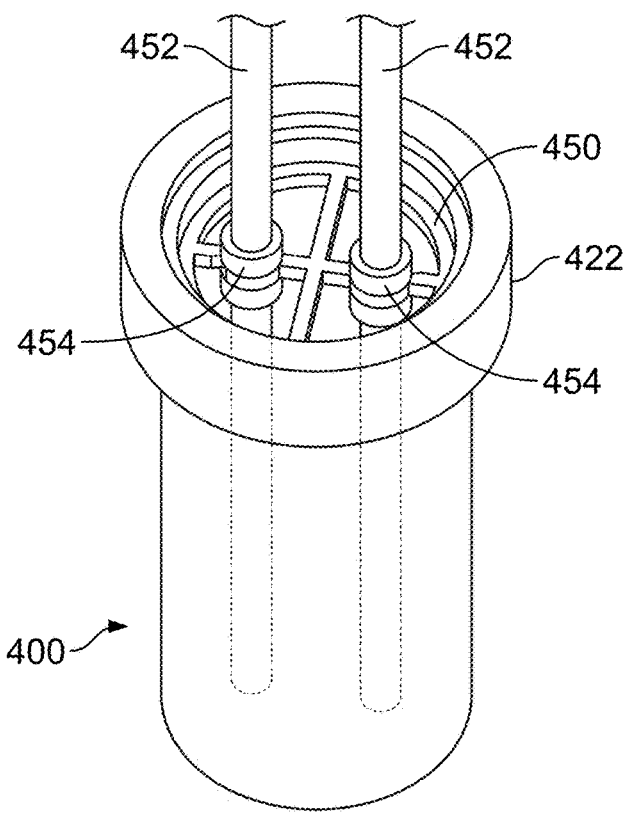
FIG. 40 illustrates a perspective end view of a hose, according to an embodiment of the present disclosure.

FIG. 40 illustrates a perspective end view of a hose, according to an embodiment of the present disclosure. A wire retainer 450 is disposed within the hose 400 and is configured to retain electrical wires 452. Strain reliefs 454 may be disposed between the wire retainer 450 and the electrical wires 452.

Figure 41:
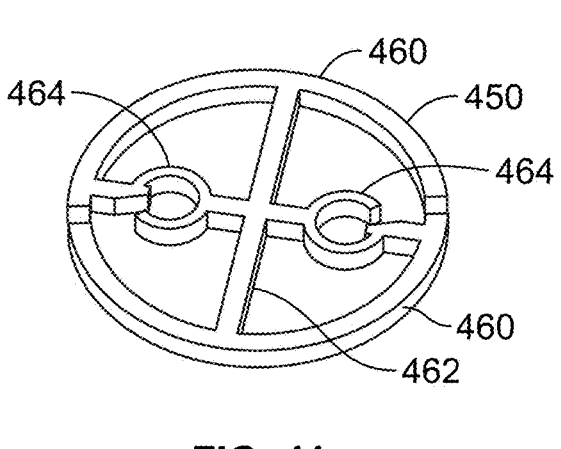
FIG. 41 illustrates a perspective top view of a wire retainer, according to an embodiment of the present disclosure.
Figure 42:
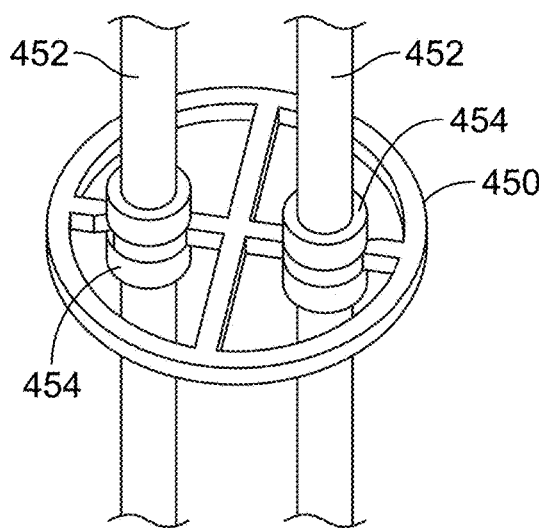
FIG. 42 illustrates a perspective view of electrical wires retained by the wire retainer, according to an embodiment of the present disclosure.

FIG. 41 illustrates a perspective top view of the wire retainer 450, according to an embodiment of the present disclosure. FIG. 42 illustrates a perspective view of the electrical wires 452 retained by the wire retainer 450. Referring to FIGS. 40-42, the wire retainer 450 includes an outer annular rim 460 that is sized and shaped to conform to an interior surface of the hose 400. The wire retainer 450 is inside the hose 400. A cross beam 462 spans across segments of the rim 460. Hose couplers 464 extend from the cross beam 462 inside of the annular rim 460. The hose couplers 464 are sized and shaped to secure around outer surfaces of the electrical wires 452.

The strain reliefs 454 can be above and below the hose couplers 464. The strain reliefs 454 can be bonded to the electrical wires 452 after the electrical wires 452 are inserted into the hose couplers 464. Optionally, the electrical wires 452 may be retained within the hose 400 through different wire retainers 450 or even without wire retainers 450.

Figure 43:
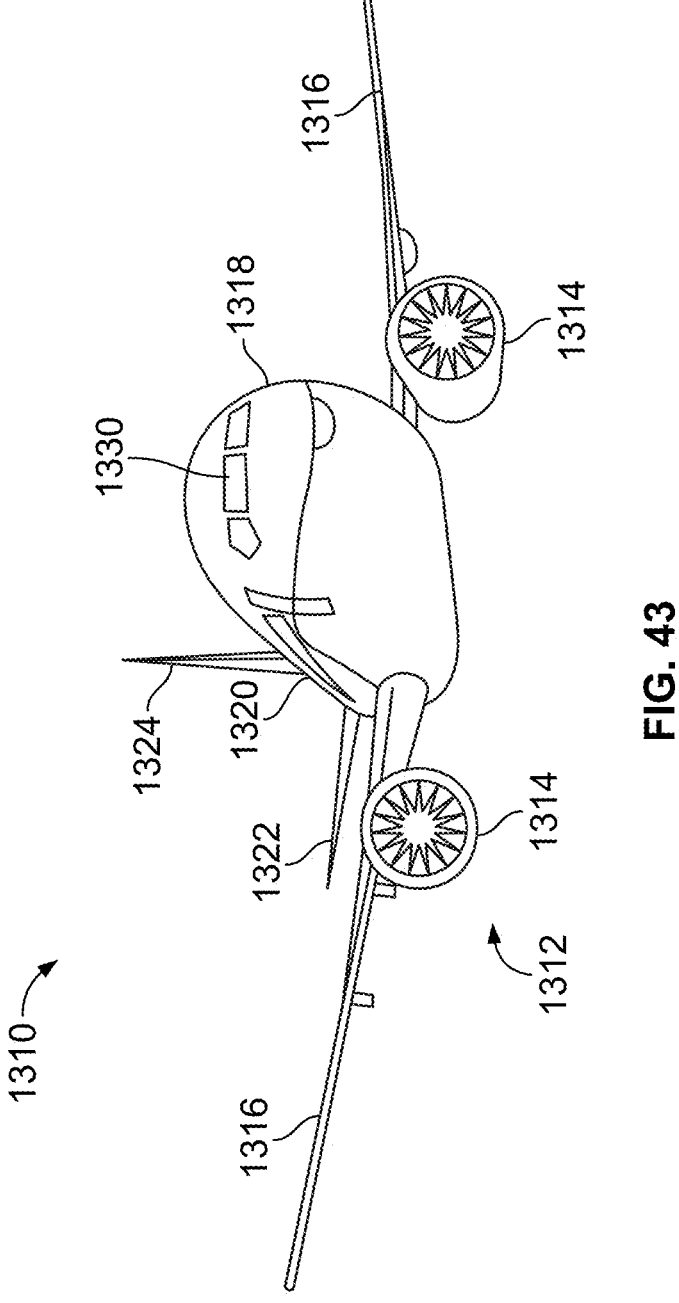
FIG. 43 illustrates a perspective front view of an aircraft, according to an embodiment of the present disclosure.

FIG. 43 illustrates a perspective front view of an aircraft 1310, according to an embodiment of the present disclosure. The aircraft 1310 includes a propulsion system 1312 that includes engines 1314, for example. Optionally, the propulsion system 1312 may include more engines 1314 than shown. The engines 1314 are carried by wings 1316 of the aircraft 1310. In other embodiments, the engines 1314 may be carried by a fuselage 1318 and/or an empennage 1320. The empennage 1320 may also support horizontal stabilizers 1322 and a vertical stabilizer 1324.

The fuselage 1318 of the aircraft 1310 defines an internal cabin 1330, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 1330 includes one or more lavatory systems, lavatory units, or lavatories, as described herein.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figures 44A, 44B:
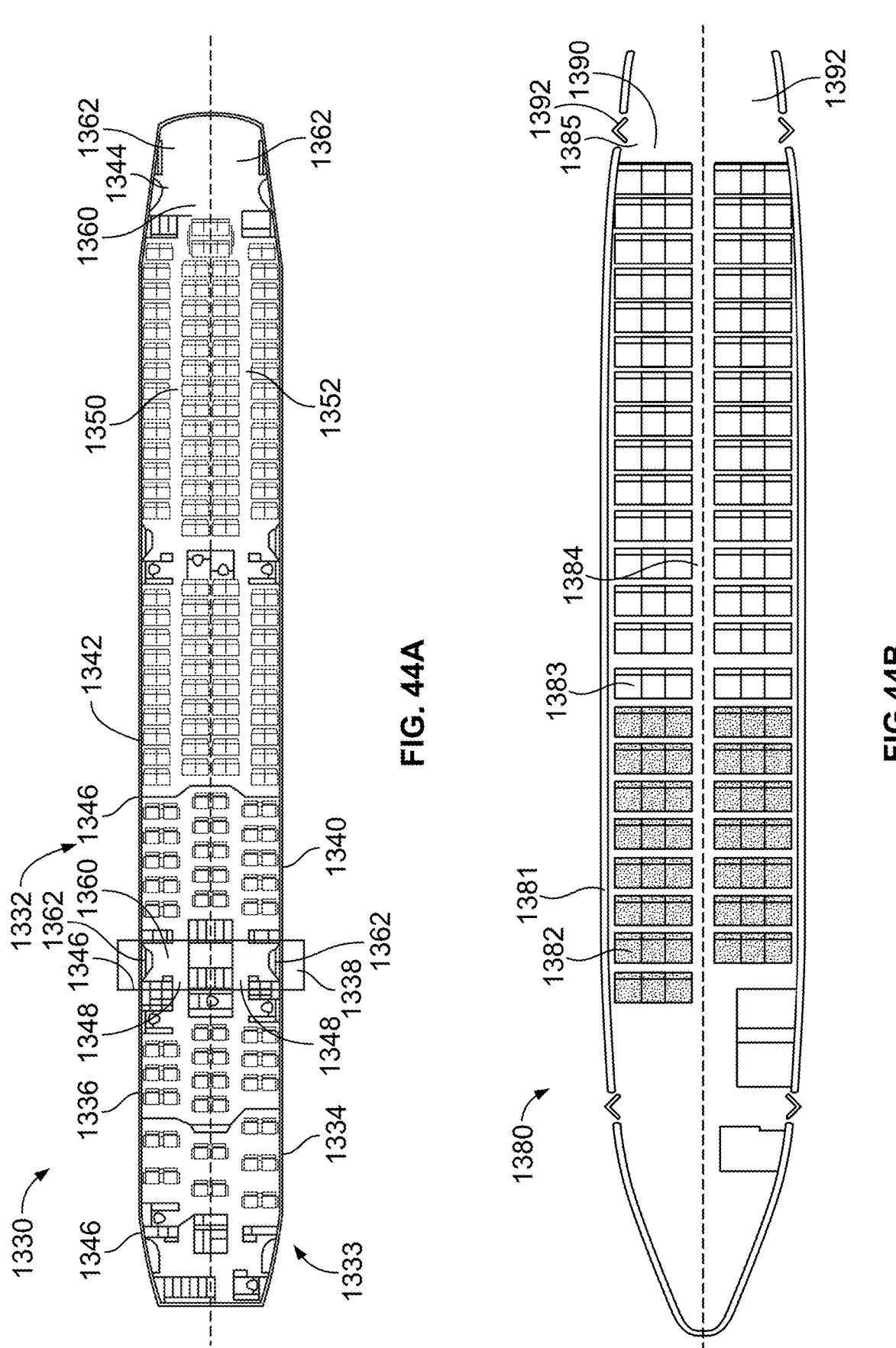
FIG. 44A illustrates a top plan view of an internal cabin of an aircraft, according to an embodiment of the present disclosure.
FIG. 44B illustrates a top plan view of an internal cabin of an aircraft, according to an embodiment of the present disclosure.

FIG. 44A illustrates a top plan view of an internal cabin 1330 of an aircraft, according to an embodiment of the present disclosure. The internal cabin 1330 may be within the fuselage 1332 of the aircraft, such as the fuselage 318 of FIG. 43. For example, one or more fuselage walls may define the internal cabin 1330. The internal cabin 1330 includes multiple sections, including a front section 1333, a first class section 1334, a business class section 1336, a front galley station 1338, an expanded economy or coach section 1340, a standard economy of coach section 1342, and an aft section 1344, which may include multiple lavatories and galley stations. It is to be understood that the internal cabin 1330 may include more or less sections than shown. For example, the internal cabin 1330 may not include a first class section, and may include more or less galley stations than shown. Each of the sections may be separated by a cabin transition area 1346, which may include class divider assemblies between aisles 1348.

As shown in FIG. 44A, the internal cabin 1330 includes two aisles 1350 and 1352 that lead to the aft section 344. Optionally, the internal cabin 1330 may have less or more aisles than shown. For example, the internal cabin 1330 may include a single aisle that extends through the center of the internal cabin 1330 that leads to the aft section 1344.

The aisles 1348, 1350, and 1352 extend to egress paths or door passageways 1360. Exit doors 1362 are located at ends of the egress paths 1360. The egress paths 1360 may be perpendicular to the aisles 1348, 1350, and 1352. The internal cabin 1330 may include more egress paths 1360 at different locations than shown. The portable sanitizing systems shown and described with respect to FIGS. 1-42 may be used to sanitize various structures within the internal cabin 1330, such as passenger seats, monuments, stowage bin assemblies, components on and within lavatories, galley equipment and components, and/or the like.

FIG. 44B illustrates a top plan view of an internal cabin 1380 of an aircraft, according to an embodiment of the present disclosure. The internal cabin 1380 is an example of the internal cabin 1330 shown in FIG. 43. The internal cabin 1380 may be within a fuselage 1381 of the aircraft. For example, one or more fuselage walls may define the internal cabin 1380. The internal cabin 1380 includes multiple sections, including a main cabin 1382 having passenger seats 1383, and an aft section 1385 behind the main cabin 1382. It is to be understood that the internal cabin 1380 may include more or less sections than shown.

The internal cabin 1380 may include a single aisle 1384 that leads to the aft section 1385. The single aisle 1384 may extend through the center of the internal cabin 1380 that leads to the aft section 1385. For example, the single aisle 1384 may be coaxially aligned with a central longitudinal plane of the internal cabin 1380.

The aisle 1384 extends to an egress path or door passageway 1390. Exit doors 1392 are located at ends of the egress path 1390. The egress path 1390 may be perpendicular to the aisle 1384. The internal cabin 1380 may include more egress paths than shown. The portable sanitizing systems shown and described with respect to FIGS. 1-42 may be used to sanitize various structures within the internal cabin 1330, such as passenger seats, monuments, stowage bin assemblies, components on and within lavatories, galley equipment and components, and/or the like.

Figure 45:
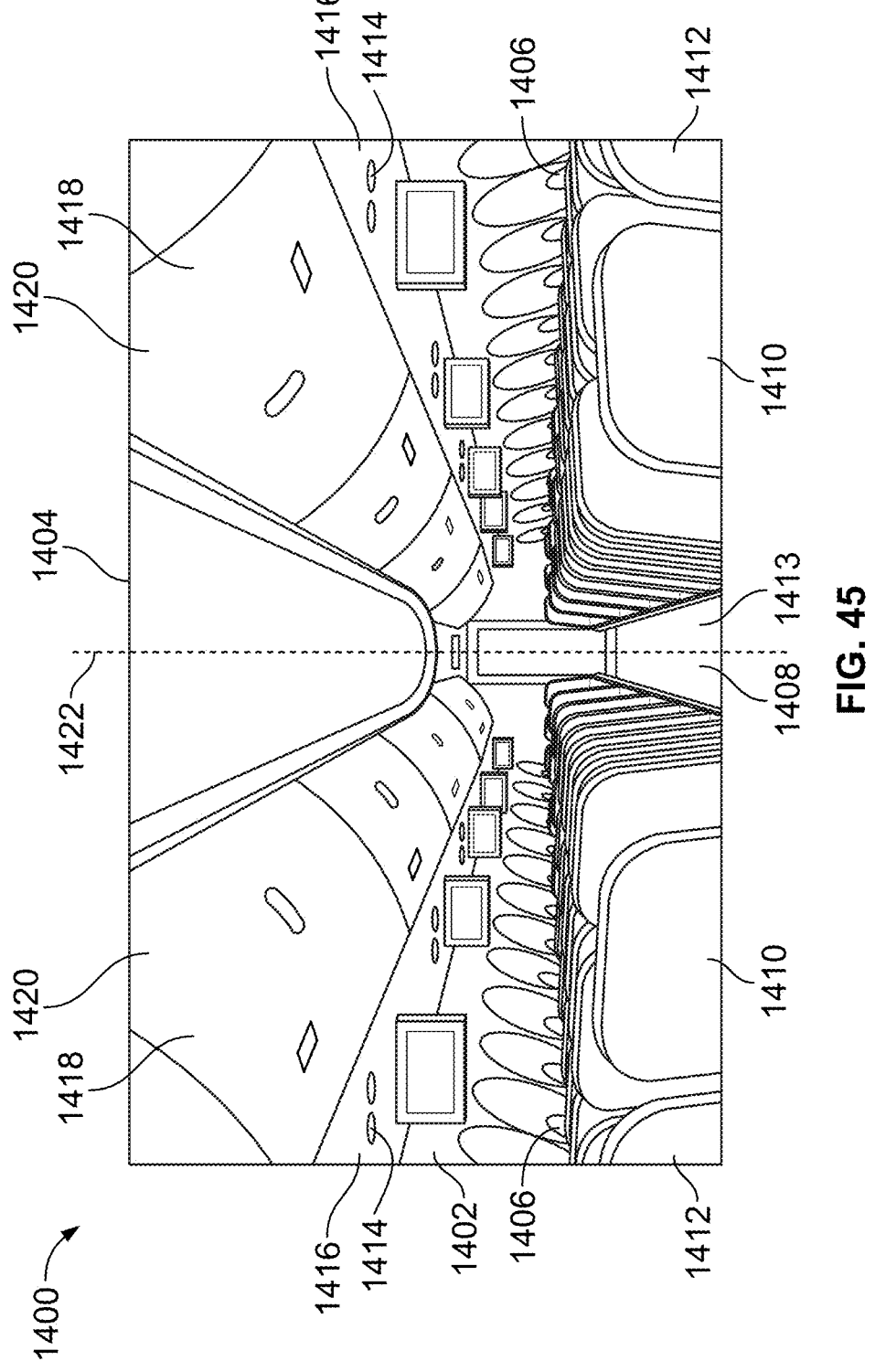
FIG. 45 illustrates a perspective interior view of an internal cabin of an aircraft, according to an embodiment of the present disclosure.

FIG. 45 illustrates a perspective interior view of an internal cabin 1400 of an aircraft, according to an embodiment of the present disclosure. The internal cabin 1400 includes outboard walls 1402 connected to a ceiling 1404. Windows 1406 may be formed within the outboard walls 1402. A floor 1408 supports rows of seats 1410. As shown in FIG. 45, a row 1412 may include two seats 1410 on either side of an aisle 1413. However, the row 1412 may include more or less seats 1410 than shown. Additionally, the internal cabin 1400 may include more aisles than shown.

Passenger service units (PSUs) 1414 are secured between an outboard wall 1402 and the ceiling 1404 on either side of the aisle 1413. The PSUs 1414 extend between a front end and rear end of the internal cabin 1400. For example, a PSU 1414 may be positioned over each seat 1410 within a row 1412. Each PSU 1414 may include a housing 1416 that generally contains vents, reading lights, an oxygen bag drop panel, an attendant request button, and other such controls over each seat 1410 (or groups of seats) within a row 1412.

Overhead stowage bin assemblies 1418 are secured to the ceiling 1404 and/or the outboard wall 1402 above and inboard from the PSU 1414 on either side of the aisle 1413. The overhead stowage bin assemblies 1418 are secured over the seats 1410. The overhead stowage bin assemblies 1418 extend between the front and rear end of the internal cabin 1400. Each stowage bin assembly 1418 may include a pivot bin or bucket 1420 pivotally secured to a strongback (hidden from view in FIG. 45). The overhead stowage bin assemblies 1418 may be positioned above and inboard from lower surfaces of the PSUs 1414. The overhead stowage bin assemblies 1418 are configured to be pivoted open in order to receive passenger carry-on baggage and personal items, for example.

As used herein, the term "outboard" means a position that is further away from a central longitudinal plane 1422 of the internal cabin 1400 as compared to another component. The term "inboard" means a position that is closer to the central longitudinal plane 1422 of the internal cabin 1400 as compared to another component. For example, a lower surface of a PSU 1414 may be outboard in relation to a stowage bin assembly 1418.

The portable sanitizing systems shown and described with respect to FIGS. 1-42 may be used to sanitize various structures shown within the internal cabin 1400.

When not in use, the portable sanitizing systems may be stored within a closet, galley cart bay, or galley cart, such as within the internal cabin of the vehicle.

Figure 46:
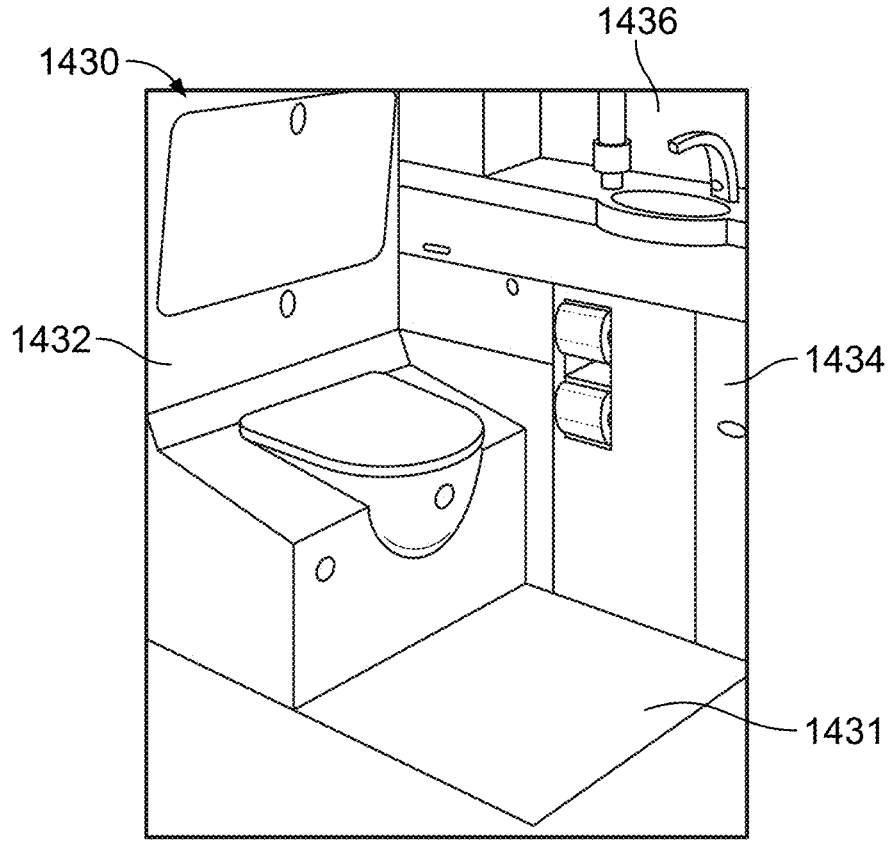
FIG. 46 illustrates a perspective internal view of a lavatory within an internal cabin of an aircraft.

FIG. 46 illustrates a perspective internal view of a lavatory 1430 within an internal cabin of a vehicle, such as any of the internal cabins described herein. The lavatory 1430 is an example of an enclosed space, monument or chamber, such as within the internal cabin a vehicle. The lavatory 1430 may be onboard an aircraft, as described above. Optionally, the lavatory 1430 may be onboard various other vehicles. In other embodiments, the lavatory 1430 may be within a fixed structure, such as a commercial or residential building. The lavatory 1430 includes a base floor 1431 that supports a toilet 1432, cabinets 1434, and a sink 1436 or wash basin. The lavatory 1430 may be arranged differently than shown. The lavatory 1430 may include more or less components than shown. The portable sanitizing systems shown and described with respect to FIGS. 1-42 may be used to sanitize the various structures, components, and surfaces within the lavatory 1430.

The portable sanitizing systems as described herein can be used to safely and effectively sanitize high-touch surfaces in the flight deck and internal cabin in a timely and cost-effective manner. UV disinfection allows the internal cabin to be quickly and effectively disinfected, such as between flights. In at least one embodiment, the portable sanitizing systems are used to augment a cleaning process, such as after manual cleaning.

Figure 47:
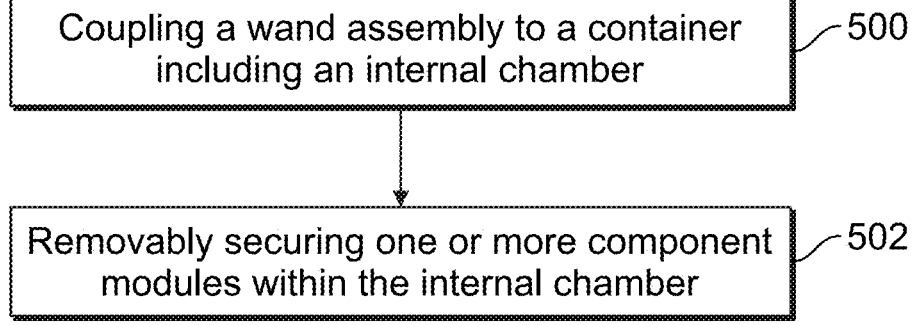
FIG. 47 illustrates a flow chart of a portable sanitizing method, according to an embodiment of the present disclosure.

FIG. 47 illustrates a flow chart of a portable sanitizing method, according to an embodiment of the present disclosure. The method include coupling, at 500, a wand assembly to a container including an internal chamber. The wand assembly includes a sanitizing head having an ultraviolet (UV) lamp. The method further includes removably securing, at 502, one or more component modules within the internal chamber.

In at least one embodiment, said removably securing includes removably securing the one or more component modules to one or more receptacles of the container through one or more coupling interfaces.

In at least one example, the method further includes disposing a radio frequency identification (RFID) tag on or within the container.

In at least one example, the method also includes disposing a global positioning system (GPS) device on or within the container.

In at least one embodiment, the method also includes disposing a window on a portion of the container.

In at least one embodiment, the one or more component modules includes a power supply. The portable sanitizing method further includes displaying status indicators on an information screen of the power supply.

As an example, the method also includes detecting, by a microcontroller of the container, information regarding the one or more component modules.

In at least one embodiment, the method also includes connecting the wand assembly to the container with a hose, and removably connecting a first connector of the hose to a second connector of the container.

In at least one embodiment, the method may be used with fixed sanitizing systems. For example, the method may be used with respect to fixed UV sanitizing systems that include UV lamps, whether or not within a wand assembly.

Further, the disclosure comprises embodiments according to the following clauses:

Clause 1. A portable sanitizing system, comprising:

a wand assembly comprising a sanitizing head having an ultraviolet (UV) lamp;

a container comprising an internal chamber, wherein the wand assembly is coupled to the container; and one or more component modules removably secured within the internal chamber.

Clause 2. The portable sanitizing system of Clause 1, wherein the container is a case assembly.

Clause 3. The portable sanitizing system of Clause 1, wherein the container is a backpack assembly.

Clause 4. The portable sanitizing system of any of Clauses 1-3, wherein the one or more component modules comprise a power supply, a battery pack, or a blower.

Clause 5. The portable sanitizing system of any of Clauses 1-4, wherein the one or more component modules include the wand assembly.

Clause 6. The portable sanitizing system of any of Clauses 1-5, wherein the container further comprises one or more receptacles within the internal chamber, and wherein the one or more component modules are configured to removably secure to the one or more receptacles through one or more coupling interfaces.

Clause 7. The portable sanitizing system of Clause 6, wherein the one or more coupling interfaces comprise a plug and a socket, one or more latches, one or more detents, or one or more snaps.

Clause 8. The portable sanitizing system of any of Clauses 1-7, wherein the container further comprises a radio frequency identification (RFID) tag.

Clause 9. The portable sanitizing system of any of Clauses 1-8, wherein the container further comprises a global positioning system (GPS) device.

Clause 10. The portable sanitizing system of any of Clauses 1-9, further comprising a retaining frame secured to the container, wherein the retaining frame is configured to house one or more additional component modules.

Clause 11. The portable sanitizing system of any of Clauses 1-10, wherein the container further comprises a window that is configured to allow viewing into at least a portion of the internal chamber.

Clause 12. The portable sanitizing system of any of Clauses 1-11, wherein the one or more component modules comprises a power supply, wherein the power supply comprises an activation switch and an information screen, and wherein status indicators are displayed on the information screen.

Clause 13. The portable sanitizing system of any of Clauses 1-12, wherein the container further comprises a microcontroller configured to detect information regarding the one or more component modules.

Clause 14. The portable sanitizing system of any of Clauses 1-13, further comprising a hose that connects the wand assembly to the container, wherein the hose comprises a first connector that removably connects to a second connector of the container.

Clause 15. A portable sanitizing method, comprising:

coupling a wand assembly to a container including an internal chamber, wherein the wand assembly includes a sanitizing head having an ultraviolet (UV) lamp; and removably securing one or more component modules within the internal chamber.

Clause 16. The portable sanitizing method of Clause 15, wherein the one or more component modules comprise a power supply, a battery pack, or a blower.

Clause 17. The portable sanitizing method of Clauses 15 or 16, wherein said removably securing comprises removably securing the one or more component modules to one or more receptacles of the container through one or more coupling interfaces.

Clause 18. The portable sanitizing method of any of Clauses 15-17, further comprising disposing a radio frequency identification (RFID) tag on or within the container.

Clause 19. The portable sanitizing method of any of Clauses 15-18, further comprising disposing a global positioning system (GPS) device on or within the container.

Clause 20. The portable sanitizing method of any of Clauses 15-19, further comprising disposing a window on a portion of the container.

Clause 21. The portable sanitizing method of any of Clauses 15-20, wherein the one or more component modules comprises a power supply, and wherein the portable sanitizing method further comprises displaying status indicators on an information screen of the power supply.

Clause 22. The portable sanitizing method of any of clauses 15-21, further comprising detecting, by a microcontroller of the container, information regarding the one or more component modules.

Clause 23. The portable sanitizing method of any of Clauses 15-22, further comprising:

connecting the wand assembly to the container with a hose; and removably connecting a first connector of the hose to a second connector of the container.

Clause 24. A portable sanitizing system, comprising:

a container comprising:

an internal chamber;

a window that is configured to allow viewing into at least a portion of the internal chamber;

a microcontroller;

a first connector; and component modules removably secured within the internal chamber, wherein the microcontroller is configured to detect information regarding the one or more component modules, and wherein the component modules comprise:

a wand assembly comprising a sanitizing head having an ultraviolet (UV) lamp;

a power supply including an activation switch and an information screen, wherein status indicators are displayed on the information screen;

a battery pack; and a blower; and a hose that connects the wand assembly to the container, wherein the hose comprises a second connector that removably connects to the first connector of the container.

As described herein, embodiments of the present disclosure provide systems and a methods for efficiently sterilizing surfaces, components, structures, and/or the like within an internal cabin of a vehicle. Further, embodiments of the present disclosure provide compact, easy-to-use, and safe systems and methods for using UV light to sterilize surfaces within an internal cabin.

As described herein, embodiments of the present disclosure provide systems and methods for quickly and easily repairing or replacing components of UV sanitizing systems. Further, embodiments of the present disclosure provide UV sanitizing system that can be easily adapted for different needs.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A portable sanitizing system, comprising:

a wand assembly comprising a sanitizing head having an ultraviolet (UV) lamp;

a container comprising:

an internal chamber and a window configured to allow viewing into at least a portion of the internal chamber;

a microcontroller; and a first connector, wherein the wand assembly is coupled to the container;

a hose coupled to the wand assembly, wherein the hose has a second connector that removably connects to the first connector of the container;

a power supply removably secured within the internal chamber;

a battery pack removably secured within the internal chamber; and a blower removably secured within the internal chamber.

2. The portable sanitizing system of claim 1, wherein the container is a case assembly.

3. The portable sanitizing system of claim 1, wherein the container is a backpack assembly.

4. The portable sanitizing system of claim 1, wherein the wand assembly is removably secured within the internal chamber.

5. The portable sanitizing system of claim 1, wherein the container further comprises one or more receptacles within the internal chamber, and wherein one or more of the wand assembly, the power supply, the battery pack, or the blower are configured to removably secure to the one or more receptacles through one or more coupling interfaces.

6. The portable sanitizing system of claim 5, wherein the one or more coupling interfaces comprise a plug and a socket, one or more latches, one or more detents, or one or more snaps.

7. The portable sanitizing system of claim 1, wherein the container further comprises a radio frequency identification (RFID) tag.

8. The portable sanitizing system of claim 1, wherein the container further comprises a global positioning system (GPS) device.

9. The portable sanitizing system of claim 1, further comprising a retaining frame secured to the container, wherein the retaining frame is configured to house one or more additional component modules.

10. The portable sanitizing system of claim 1, wherein the power supply comprises an activation switch and an information screen, and wherein status indicators are displayed on the information screen.

11. The portable sanitizing system of claim 1, wherein the microcontroller is configured to detect information regarding one or more of the wand assembly, the power supply, the battery pack, or the blower.

12. A portable sanitizing method for a portable sanitizing system, comprising:

a wand assembly comprising a sanitizing head having an ultraviolet (UV) lamp;

a container comprising:

an internal chamber and a window configured to allow viewing into at least a portion of the internal chamber;

a microcontroller; and a first connector, wherein the wand assembly is coupled to the container;

a hose coupled to the wand assembly, wherein the hose has a second connector that removably connects to the first connector of the container;

a power supply removably secured within the internal chamber;

a battery pack removably secured within the internal chamber; and a blower removably secured within the internal chamber, the portable sanitizing method comprising:

coupling the wand assembly to the container including the internal chamber; and removably securing the power supply, the battery pack, and the blower within the internal chamber.

13. The portable sanitizing method of claim 12, wherein said removably securing comprises removably securing one or more of the power supply, the battery pack, or the blower to one or more receptacles of the container through one or more coupling interfaces.

14. The portable sanitizing method of claim 12, further comprising disposing a radio frequency identification (RFID) tag on or within the container.

15. The portable sanitizing method of claim 12, further comprising disposing a global positioning system (GPS) device on or within the container.

16. The portable sanitizing method of claim 12, further comprising displaying status indicators on an information screen of the power supply.

17. The portable sanitizing method of claim 12, further comprising detecting, by the microcontroller of the container, information regarding one or more of the wand assembly, the power supply, the battery pack, or the blower.

18. The portable sanitizing method of claim 12, further comprising:

connecting the wand assembly to the container with the hose; and removably connecting a first connector of the hose to a second connector of the container.

19. A portable sanitizing system, comprising:

a container comprising:

an internal chamber;

a window that is configured to allow viewing into at least a portion of the internal chamber;

a microcontroller; and a first connector; and component modules removably secured within the internal chamber, wherein the microcontroller is configured to detect information regarding the one or more component modules, and wherein the component modules comprise:

a wand assembly comprising a sanitizing head having an ultraviolet (UV) lamp;

a power supply including an activation switch and an information screen, wherein status indicators are displayed on the information screen;

a battery pack; and a blower; and a hose that connects the wand assembly to the container, wherein the hose comprises a second connector that removably connects to the first connector of the container.

20. The portable sanitizing system of claim 19, wherein the container is a case assembly.

21. The portable sanitizing system of claim 19, wherein the container is a backpack assembly.

22. The portable sanitizing system of claim 19, wherein the container further comprises one or more receptacles within the internal chamber, and wherein the one or more component modules are configured to removably secure to the one or more receptacles through one or more coupling interfaces.

23. The portable sanitizing system of claim 22, wherein the one or more coupling interfaces comprise a plug and a socket, one or more latches, one or more detents, or one or more snaps.

24. The portable sanitizing system of claim 19, further comprising a retaining frame secured to the container, wherein the retaining frame is configured to house one or more additional component modules.

* * * * *